(12) United States Patent
Miyagi et al.

(10) Patent No.: US 11,091,545 B2
(45) Date of Patent: Aug. 17, 2021

(54) METHODS OF USING AN ANTIBODY TO STABILIZE AND ANALYZE A BRIL FUSION PROTEIN

(71) Applicant: KYOWA KIRIN CO., LTD., Tokyo (JP)

(72) Inventors: Hikaru Miyagi, Tokyo (JP); Michihiko Suzuki, Tokyo (JP); Junichi Saito, Tokyo (JP); Hidetsugu Asada, Kyoto (JP); So Iwata, Kyoto (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 0 days.

(21) Appl. No.: 16/630,181

(22) PCT Filed: Jul. 12, 2018

(86) PCT No.: PCT/JP2018/026408
§ 371 (c)(1),
(2) Date: Jan. 10, 2020

(87) PCT Pub. No.: WO2019/013308
PCT Pub. Date: Jan. 17, 2019

(65) Prior Publication Data
US 2020/0157211 A1    May 21, 2020

(30) Foreign Application Priority Data

Jul. 13, 2017    (JP) .............................. JP2017-137269

(51) Int. Cl.
*C07K 16/28*    (2006.01)
*C07K 14/705*    (2006.01)
*C07K 14/72*    (2006.01)

(52) U.S. Cl.
CPC ............ *C07K 16/28* (2013.01); *C07K 14/705* (2013.01); *C07K 14/723* (2013.01); *C07K 2317/565* (2013.01); *C07K 2319/30* (2013.01); *C07K 2319/35* (2013.01)

(58) Field of Classification Search
CPC ...... C07K 16/00; C07K 16/28; C07K 14/705; C07K 14/723; C07K 2317/565; C07K 2319/30; C07K 2319/35; C07K 19/00; C12N 15/09
See application file for complete search history.

(56) References Cited

U.S. PATENT DOCUMENTS

| 6,107,035 A | 8/2000 | Squires et al. |
| 2009/0075290 A1 | 3/2009 | Aoyama |
| 2012/0288913 A1 | 11/2012 | Hanson et al. |

FOREIGN PATENT DOCUMENTS

| JP | 2014-516963 | 7/2014 |
| WO | 2006/112445 | 12/2006 |
| WO | 2012/148586 | 11/2012 |
| WO | 2012/158555 | 11/2012 |
| WO | 2015/148984 | 10/2015 |

OTHER PUBLICATIONS

Mavridou DA, et al. (Nov. 24, 2011) The Journal Of Biological Chemistry. 287(4):2342-2352. (doi: 10.1074/jbc.m111.313692).*
Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983.*
Colman, PM (1994) Research in Immunology, Elsevier, NY, 145(1):33-36.*
Pebay-Peyroula et al., "X-ray Structure of Bacteriorhodopsin at 2.5 Angstroms from Microcrystals Grown in Lipidic Cubic Phases", Science, 1997, vol. 277, pp. 1676-1681.
Palczewski et al., "Crystal Structure of Rhodopsin: A G Protein-Coupled Receptor", Science, 2000, vol. 289, No. 5480, pp. 739-745.
Rosenbaum et al., "GPCR Engineering Yields High-Resolution Structural Insights into $\beta_2$-Adrenergic Receptor Function", Science, 2007, vol. 318, pp. 1266-1273.
Chun et al., "Fusion Partner Toolchest for the Stabilization and Crystallization of G Protein-Coupled Receptors", Structure, 2012, vol. 20, No. 6, pp. 967-976.
Serrano-Vega et al., "Conformational thermostabilization of the $\beta$1-adrenergic receptor in a detergent-resistant form", PNAS, 2008, vol. 105, No. 3, pp. 877-882.
Hino et al., "G Protein-coupled receptor inactivation by an allosteric inverse-agonist antibody", Nature, 2012, vol. 482, No. 7384, pp. 237-240.
Sun et al., "Crystal structure of the adenosine $A_{2A}$ receptor bound to an antagonist reveals a potential allosteric pocket", PNAS, 2017, vol. 114, No. 8, pp. 2066-2071.
Ku et al., "Alternate protein frameworks for molecular recognition", Proceedings of the National Academy of Science USA, 1995, vol. 92, pp. 6552-6556.
International Search Report dated Oct. 9, 2018 in International (PCT) Patent Application No. PCT/JP2018/026408, with English Translation.
Written Opinion of the International Searching Authority dated Oct. 9, 2018 in International (PCT) Patent Application No. PCT/JP2018/026408, with English Translation.

(Continued)

*Primary Examiner* — Robert S Landsman
(74) *Attorney, Agent, or Firm* — Wenderoth, Lind & Ponack, L.L.P.

(57) ABSTRACT

An object of the present invention is to provide a method of enabling efficient structural analysis of a target protein that has been impossible or difficult to analyze so far, by stabilizing the target protein. The present invention provides an anti-BRIL antibody which specifically binds to BRIL or a BRIL fusion protein and an antigen-binding fragment thereof, a nucleic acid encoding the anti-BRIL antibody and the antigen-binding fragment thereof, a vector containing the nucleic acid, an antibody producing cell containing the vector, a method of producing the antibody, and a method of using the antibody in a protein structural analysis.

7 Claims, 5 Drawing Sheets

Specification includes a Sequence Listing.

(56) References Cited

OTHER PUBLICATIONS

Extended European Search Report dated Feb. 25, 2021 in corresponding European Patent Application No. 18832377.8.
Rasmussen et al., "Structure of a nanobody-stabilized active state of the $\beta_2$ adrenoceptor", Nature, 2011, vol. 469, No. 7329,13, pp. 175-180.
Cheng et al., "Structural insight into allosteric modulation of protease-activated receptor 2", Nature, 2017, vol. 545, No. 7652,4, pp. 112-115.

* cited by examiner

SEQUENCE LISTING

```
<160> NUMBER OF SEQ ID NOS: 18

<210> SEQ ID NO 1
<211> LENGTH: 5
<212> TYPE: PRT
<213> ORGANISM: Mus musculus

<400> SEQUENCE: 1

Asp Phe Tyr Ile Asn
1               5

<210> SEQ ID NO 2
<211> LENGTH: 17
<212> TYPE: PRT
<213> ORGANISM: Mus musculus

<400> SEQUENCE: 2

Trp Ile Phe Pro Gly Ser Gly Asn Thr His Tyr Asn Glu Lys Phe Lys
1               5                   10                  15

Gly

<210> SEQ ID NO 3
<211> LENGTH: 10
<212> TYPE: PRT
<213> ORGANISM: Mus musculus

<400> SEQUENCE: 3

Pro Val Ser Tyr Tyr Tyr Asp Phe Asp Tyr
1               5                   10
```

```
<210> SEQ ID NO 4
<211> LENGTH: 11
<212> TYPE: PRT
<213> ORGANISM: Mus musculus

<400> SEQUENCE: 4

Arg Ala Ser Gln Ser Val Ser Asn Tyr Leu His
1               5                   10

<210> SEQ ID NO 5
<211> LENGTH: 7
<212> TYPE: PRT
<213> ORGANISM: Mus musculus

<400> SEQUENCE: 5

Tyr Ala Ser Gln Ser Ile Ser
1               5

<210> SEQ ID NO 6
<211> LENGTH: 9
<212> TYPE: PRT
<213> ORGANISM: Mus musculus

<400> SEQUENCE: 6

Gln Gln Ser Asn Ser Trp Pro Leu Thr
1               5

<210> SEQ ID NO 7
<211> LENGTH: 119
<212> TYPE: PRT
<213> ORGANISM: Mus musculus

<400> SEQUENCE: 7

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Phe
            20                  25                  30

Tyr Ile Asn Trp Met Lys Gln Arg Pro Gly Gln Gly Leu Glu Trp Ile
        35                  40                  45

Gly Trp Ile Phe Pro Gly Ser Gly Asn Thr His Tyr Asn Glu Lys Phe
    50                  55                  60

Lys Gly Lys Ala Thr Leu Ile Val Asp Thr Ser Ser Ser Thr Ala Phe
65                  70                  75                  80

Met Gln Leu Asn Ser Leu Thr Ser Glu Asp Ser Ala Val Tyr Phe Cys
                85                  90                  95

Thr Arg Pro Val Ser Tyr Tyr Tyr Asp Phe Asp Tyr Trp Gly Gln Gly
            100                 105                 110

Thr Thr Leu Thr Val Ser Ser
        115

<210> SEQ ID NO 8
<211> LENGTH: 107
<212> TYPE: PRT
<213> ORGANISM: Mus musculus

<400> SEQUENCE: 8

Asp Ile Val Leu Thr Gln Ser Pro Ala Thr Leu Ser Val Thr Pro Gly
1               5                   10                  15

Asp Arg Val Ser Leu Ser Cys Arg Ala Ser Gln Ser Val Ser Asn Tyr
            20                  25                  30
```

```
Leu His Trp Tyr Gln Gln Lys Ser His Glu Ser Pro Arg Leu Leu Ile
             35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Ser Asn Ser Trp Pro Leu
                 85                  90                  95

Thr Phe Gly Ala Gly Thr Lys Leu Glu Leu Arg
                100                 105
```

<210> SEQ ID NO 9
<211> LENGTH: 106
<212> TYPE: PRT
<213> ORGANISM: Artificial
<220> FEATURE:
<223> OTHER INFORMATION: Description of the artificial sequence: amino
      acid sequence of BRIL

<400> SEQUENCE: 9

```
Ala Asp Leu Glu Asp Asn Trp Glu Thr Leu Asn Asp Asn Leu Lys Val
 1               5                   10                  15

Ile Glu Lys Ala Asp Asn Ala Ala Gln Val Lys Asp Ala Leu Thr Lys
             20                  25                  30

Met Arg Ala Ala Ala Leu Asp Ala Gln Lys Ala Thr Pro Pro Lys Leu
         35                  40                  45

Glu Asp Lys Ser Pro Asp Ser Pro Glu Met Lys Asp Phe Arg His Gly
 50                  55                  60

Phe Asp Ile Leu Val Gly Gln Ile Asp Asp Ala Leu Lys Leu Ala Asn
 65                  70                  75                  80

Glu Gly Lys Val Lys Glu Ala Gln Ala Ala Ala Glu Gln Leu Lys Thr
                 85                  90                  95

Thr Arg Asn Ala Tyr Ile Gln Lys Tyr Leu
                100                 105
```

<210> SEQ ID NO 10
<211> LENGTH: 373
<212> TYPE: PRT
<213> ORGANISM: Homo sapiens

<400> SEQUENCE: 10

```
Met Arg Met Glu Asp Glu Asp Tyr Asn Thr Ser Ile Ser Tyr Gly Asp
 1               5                   10                  15

Glu Tyr Pro Asp Tyr Leu Asp Ser Ile Val Val Leu Glu Asp Leu Ser
             20                  25                  30

Pro Leu Glu Ala Arg Val Thr Arg Ile Phe Leu Val Val Val Tyr Ser
         35                  40                  45

Ile Val Cys Phe Leu Gly Ile Leu Gly Asn Gly Leu Val Ile Ile Ile
 50                  55                  60

Ala Thr Phe Lys Met Lys Lys Thr Val Asn Met Val Trp Phe Leu Asn
 65                  70                  75                  80

Leu Ala Val Ala Asp Phe Leu Phe Asn Val Phe Leu Pro Ile His Ile
                 85                  90                  95

Thr Tyr Ala Ala Met Asp Tyr His Trp Val Phe Gly Thr Ala Met Cys
                100                 105                 110

Lys Ile Ser Asn Phe Leu Leu Ile His Asn Met Phe Thr Ser Val Phe
                115                 120                 125
```

-continued

Leu Leu Thr Ile Ile Ser Ser Asp Arg Cys Ile Ser Val Leu Leu Pro
            130                 135                 140

Val Trp Ser Gln Asn His Arg Ser Val Arg Leu Ala Tyr Met Ala Cys
145                 150                 155                 160

Met Val Ile Trp Val Leu Ala Phe Phe Leu Ser Ser Pro Ser Leu Val
                165                 170                 175

Phe Arg Asp Thr Ala Asn Leu His Gly Lys Ile Ser Cys Phe Asn Asn
            180                 185                 190

Phe Ser Leu Ser Thr Pro Gly Ser Ser Trp Pro Thr His Ser Gln
            195                 200                 205

Met Asp Pro Val Gly Tyr Ser Arg His Met Val Thr Val Thr Arg
210                 215                 220

Phe Leu Cys Gly Phe Leu Val Pro Val Leu Ile Ile Thr Ala Cys Tyr
225                 230                 235                 240

Leu Thr Ile Val Cys Lys Leu Gln Arg Asn Arg Leu Ala Lys Thr Lys
                245                 250                 255

Lys Pro Phe Lys Ile Ile Val Thr Ile Ile Ile Thr Phe Phe Leu Cys
            260                 265                 270

Trp Cys Pro Tyr His Thr Leu Asn Leu Leu Glu Leu His His Thr Ala
            275                 280                 285

Met Pro Gly Ser Val Phe Ser Leu Gly Leu Pro Leu Ala Thr Ala Leu
290                 295                 300

Ala Ile Ala Asn Ser Cys Met Asn Pro Ile Leu Tyr Val Phe Met Gly
305                 310                 315                 320

Gln Asp Phe Lys Lys Phe Lys Val Ala Leu Phe Ser Arg Leu Val Asn
                325                 330                 335

Ala Leu Ser Glu Asp Thr Gly His Ser Ser Tyr Pro Ser His Arg Ser
            340                 345                 350

Phe Thr Lys Met Ser Ser Met Asn Glu Arg Thr Ser Met Asn Glu Arg
            355                 360                 365

Glu Thr Gly Met Leu
        370

<210> SEQ ID NO 11
<211> LENGTH: 416
<212> TYPE: PRT
<213> ORGANISM: Artificial
<220> FEATURE:
<223> OTHER INFORMATION: Description of the artificial sequence:
      hChemR23-BRIL fusion protein

<400> SEQUENCE: 11

Ser Pro Leu Glu Ala Arg Val Thr Arg Ile Phe Leu Val Val Val Tyr
1               5                   10                  15

Ser Ile Val Cys Phe Leu Gly Ile Leu Gly Asn Gly Leu Val Ile Ile
                20                  25                  30

Ile Ala Thr Phe Lys Met Lys Lys Thr Val Asn Met Val Trp Phe Leu
            35                  40                  45

Asn Leu Ala Val Ala Asp Phe Leu Phe Asn Val Phe Leu Pro Ile His
50                  55                  60

Ile Thr Tyr Ala Ala Met Asp Tyr His Trp Val Phe Gly Thr Ala Met
65                  70                  75                  80

Cys Lys Ile Ser Asn Phe Leu Leu Ile His Asn Met Phe Thr Ser Val
                85                  90                  95

Phe Leu Leu Thr Ile Ile Ser Ser Asp Arg Cys Ile Ser Val Leu Leu
                100                 105                 110

Pro Val Trp Ser Gln Asn His Arg Ser Val Arg Leu Ala Tyr Met Ala
            115                 120                 125

Cys Met Val Ile Trp Val Leu Ala Phe Phe Leu Ser Ser Pro Ser Leu
        130                 135                 140

Val Phe Arg Asp Thr Ala Asn Leu His Gly Lys Ile Ser Cys Phe Asn
145                 150                 155                 160

Asn Phe Ser Leu Ser Thr Pro Gly Ser Ser Trp Pro Thr His Ser
            165                 170                 175

Gln Met Asp Pro Val Gly Tyr Ser Arg His Met Val Thr Val Thr
            180                 185                 190

Arg Phe Leu Cys Gly Phe Leu Val Pro Val Leu Ile Ile Thr Ala Cys
            195                 200                 205

Tyr Leu Thr Ile Val Cys Lys Leu Gln Arg Asn Arg Ala Asp Leu Glu
        210                 215                 220

Asp Asn Trp Glu Thr Leu Asn Asp Asn Leu Lys Val Ile Glu Lys Ala
225                 230                 235                 240

Asp Asn Ala Ala Gln Val Lys Asp Ala Leu Thr Lys Met Arg Ala Ala
            245                 250                 255

Ala Leu Asp Ala Gln Lys Ala Thr Pro Pro Lys Leu Glu Asp Lys Ser
            260                 265                 270

Pro Asp Ser Pro Glu Met Lys Asp Phe Arg His Gly Phe Asp Ile Leu
        275                 280                 285

Val Gly Gln Ile Asp Asp Ala Leu Lys Leu Ala Asn Glu Gly Lys Val
        290                 295                 300

Lys Glu Ala Gln Ala Ala Ala Glu Gln Leu Lys Thr Thr Arg Asn Ala
305                 310                 315                 320

Tyr Ile Gln Lys Tyr Leu Ala Lys Thr Lys Pro Phe Lys Ile Ile
            325                 330                 335

Val Thr Ile Ile Ile Thr Phe Phe Leu Cys Trp Cys Pro Tyr His Thr
            340                 345                 350

Leu Asn Leu Leu Glu Leu His His Thr Ala Met Pro Gly Ser Val Phe
        355                 360                 365

Ser Leu Gly Leu Pro Leu Ala Thr Ala Leu Ala Ile Ala Asn Ser Cys
        370                 375                 380

Met Asn Pro Ile Leu Tyr Val Phe Met Gly Gln Asp Phe Lys Lys Phe
385                 390                 395                 400

Lys Val Ala Leu Phe Ser Arg Leu Val Asn Ala Leu Ser Glu Asp Thr
            405                 410                 415

<210> SEQ ID NO 12
<211> LENGTH: 376
<212> TYPE: PRT
<213> ORGANISM: Artificial
<220> FEATURE:
<223> OTHER INFORMATION: Description of the artificial sequence:
      hCCR10-BRIL fusion protein

<400> SEQUENCE: 12

Ser Arg Ala Phe Gln Pro Ser Val Ser Leu Thr Val Ala Ala Leu Gly
1               5                   10                  15

Leu Ala Gly Asn Gly Leu Val Leu Ala Thr His Leu Ala Ala Arg Arg
            20                  25                  30

Ala Ala Arg Ser Pro Thr Ser Ala His Leu Leu Gln Leu Ala Leu Ala
        35                  40                  45

Asp Leu Leu Leu Ala Leu Thr Leu Pro Phe Ala Ala Ala Gly Ala Leu

```
            50                  55                  60
Gln Gly Trp Ser Leu Gly Ser Ala Thr Cys Arg Thr Ile Ser Gly Leu
 65                  70                  75                  80

Tyr Ser Ala Ser Phe His Ala Gly Phe Leu Phe Leu Ala Cys Ile Ser
                 85                  90                  95

Ala Asp Arg Tyr Val Ala Ile Ala Arg Ala Leu Pro Ala Gly Pro Arg
                100                 105                 110

Pro Ser Thr Pro Gly Arg Ala His Leu Val Ser Val Ile Val Trp Leu
            115                 120                 125

Leu Ser Leu Leu Leu Ala Leu Pro Ala Leu Leu Phe Ser Gln Asp Gly
        130                 135                 140

Gln Arg Glu Gly Gln Arg Arg Cys Arg Leu Ile Phe Pro Glu Gly Leu
145                 150                 155                 160

Thr Gln Thr Val Lys Gly Ala Ser Ala Val Ala Gln Val Ala Leu Gly
                165                 170                 175

Phe Ala Leu Pro Leu Gly Val Met Val Ala Cys Tyr Ala Leu Leu Gly
            180                 185                 190

Arg Thr Leu Leu Ala Ala Asp Leu Glu Asp Asn Trp Glu Thr Leu Asn
        195                 200                 205

Asp Asn Leu Lys Val Ile Glu Lys Ala Asp Asn Ala Ala Gln Val Lys
210                 215                 220

Asp Ala Leu Thr Lys Met Arg Ala Ala Ala Leu Asp Ala Gln Lys Ala
225                 230                 235                 240

Thr Pro Pro Lys Leu Glu Asp Lys Ser Pro Asp Ser Pro Glu Met Lys
                245                 250                 255

Asp Phe Arg His Gly Phe Asp Ile Leu Val Gly Gln Ile Asp Asp Ala
            260                 265                 270

Leu Lys Leu Ala Asn Glu Gly Lys Val Lys Glu Ala Gln Ala Ala Ala
        275                 280                 285

Glu Gln Leu Lys Thr Thr Arg Asn Ala Tyr Ile Gln Lys Tyr Leu Arg
290                 295                 300

Arg Ala Leu Arg Val Val Ala Leu Val Ala Ala Phe Val Val Leu
305                 310                 315                 320

Gln Leu Pro Tyr Ser Leu Ala Leu Leu Leu Asp Thr Ala Asp Leu Leu
                325                 330                 335

Ala Ala Arg Glu Arg Ser Cys Pro Ala Ser Lys Arg Lys Asp Val Ala
            340                 345                 350

Leu Leu Val Thr Ser Gly Leu Ala Leu Ala Arg Cys Gly Leu Asn Pro
        355                 360                 365

Val Leu Tyr Ala Phe Leu Gly Leu
        370                 375

<210> SEQ ID NO 13
<211> LENGTH: 357
<212> TYPE: DNA
<213> ORGANISM: Mus musculus

<400> SEQUENCE: 13
cagatccagc tgcagcagtc tggacctgag ctggtgaagc ctggggcttc agtgaagata      60
tcctgcaagg cttctggcta caccttcact gacttctata aaactggat  gaagcagagg     120 cctggacagg gacttgagtg gattggatgg atttttcctg gaagcggtaa tactcactac     180
aatgagaagt tcaagggcaa ggccacattg attgtagaca catcctccag cacagccttc     240
atgcagctca acagcctgac ctctgaggac tctgcggtct atttctgtac aagaccggtc     300
```
tcttattact acgattttga ctactggggc caaggcacca ctctcacagt ctcctca    357

<210> SEQ ID NO 14
<211> LENGTH: 321
<212> TYPE: DNA
<213> ORGANISM: Mus musculus

<400> SEQUENCE: 14
gatattgtgc taactcagtc tccagccacc ctgtctgtga ctccaggaga tagagtcagt     60
ctttcctgca gggccagcca agtgttagc aactacctac actggtatca acaaaaatca    120
catgagtctc caaggcttct catcaagtat gcttcccagt ccatctctgg gatcccctcc    180
aggttcagtg gcagtggatc aggacagat ttcactctca gtatcaacag tgtggagact    240
gaagattttg gaatgtattt ctgtcaacag agtaacagct ggccgctcac gttcggtgct    300
gggaccaagc tggagctgag a                                              321

<210> SEQ ID NO 15
<211> LENGTH: 138
<212> TYPE: PRT
<213> ORGANISM: Mus musculus

<400> SEQUENCE: 15

Met Gly Trp Ser Trp Ile Phe Leu Phe Leu Leu Ser Gly Thr Ala Gly
1               5                   10                  15

Val His Cys Gln Ile Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Phe Tyr Ile Asn Trp Met Lys Gln Arg Pro Gly Gln Gly Leu
    50                  55                  60

Glu Trp Ile Gly Trp Ile Phe Pro Gly Ser Gly Asn Thr His Tyr Asn
65                  70                  75                  80

Glu Lys Phe Lys Gly Lys Ala Thr Leu Ile Val Asp Thr Ser Ser Ser
                85                  90                  95

Thr Ala Phe Met Gln Leu Asn Ser Leu Thr Ser Glu Asp Ser Ala Val
            100                 105                 110

Tyr Phe Cys Thr Arg Pro Val Ser Tyr Tyr Asp Phe Asp Tyr Trp
        115                 120                 125

Gly Gln Gly Thr Thr Leu Thr Val Ser Ser
    130                 135

<210> SEQ ID NO 16
<211> LENGTH: 127
<212> TYPE: PRT
<213> ORGANISM: Mus musculus

<400> SEQUENCE: 16

Met Val Phe Thr Pro Gln Ile Leu Gly Leu Met Leu Phe Trp Ile Ser
1               5                   10                  15

Ala Ser Arg Gly Asp Ile Val Leu Thr Gln Ser Pro Ala Thr Leu Ser
            20                  25                  30

Val Thr Pro Gly Asp Arg Val Ser Leu Ser Cys Arg Ala Ser Gln Ser
        35                  40                  45

Val Ser Asn Tyr Leu His Trp Tyr Gln Gln Lys Ser His Glu Ser Pro
    50                  55                  60

Arg Leu Leu Ile Lys Tyr Ala Ser Gln Ser Ile Ser Gly Ile Pro Ser

-continued

```
                65                  70                  75                  80
Arg Phe Ser Gly Ser Gly Ser Gly Thr Asp Phe Thr Leu Ser Ile Asn
                    85                  90                  95

Ser Val Glu Thr Glu Asp Phe Gly Met Tyr Phe Cys Gln Gln Ser Asn
                    100                 105                 110

Ser Trp Pro Leu Thr Phe Gly Ala Gly Thr Lys Leu Glu Leu Arg
                    115                 120                 125

<210> SEQ ID NO 17
<211> LENGTH: 414
<212> TYPE: DNA
<213> ORGANISM: Mus musculus

<400> SEQUENCE: 17
atgggatgga gctggatctt tcttttcctc ctgtcaggaa ctgcaggtgt ccattgccag       60
atccagctgc agcagtctgg acctgagctg gtgaagcctg gggcttcagt gaagatatcc     120
tgcaaggctt ctggctacac cttcactgac ttctatataa actggatgaa gcagaggcct     180
ggacagggac ttgagtggat tggatggatt tttcctggaa gcggtaatac tcactacaat     240
gagaagttca agggcaaggc cacattgatt gtagacacat cctccagcac agccttcatg     300
cagctcaaca gcctgacctc tgaggactct gcggtctatt tctgtacaag accggtctct     360
tattactacg attttgacta ctggggccaa ggcaccactc tcacagtctc ctca           414

<210> SEQ ID NO 18
<211> LENGTH: 381
<212> TYPE: DNA
<213> ORGANISM: Mus musculus

<400> SEQUENCE: 18
atggttttca cacctcagat tcttggactt atgcttttct ggatttcagc ctccagaggt      60
gatattgtgc taactcagtc tccagccacc ctgtctgtga ctccaggaga tagagtcagt     120
ctttcctgca gggccagcca aagtgttagc aactacctac actggtatca acaaaaatca     180
catgagtctc caaggcttct catcaagtat gcttcccagt ccatctctgg gatcccctcc     240
aggttcagtg gcagtggatc agggacagat ttcactctca gtatcaacag tgtggagact     300
gaagattttg gaatgtattt ctgtcaacag agtaacagct ggccgctcac gttcggtgct     360
gggaccaagc tggagctgag a                                               381
```

METHODS OF USING AN ANTIBODY TO STABILIZE AND ANALYZE A BRIL FUSION PROTEIN

TECHNICAL FIELD

The present invention relates to a method of stabilizing BRIL fusion protein using an anti-BRIL antibody, a method of crystalizing the BRIL fusion protein using the anti-BRIL antibody, a method of producing and preparing crystal using the anti-BRIL antibody, a method of analyzing a crystal structure of the BRIL fusion protein using the anti-BRIL antibody, the anti-BRIL antibody, nucleic acid encoding the antibody thereof, a vector containing the nucleic acid, a transformed cell into which the vector is introduced, and a method of producing the anti-BRIL antibody.

BACKGROUND ART

Proteins that play an essential role in life are involved in many diseases, and in particular, G protein-coupled receptors (GPCRs) play important functions in signal transduction, and are target proteins of more than 30% pharmaceutical products. In current drug discovery, screening of candidate compounds and design of new compounds are carried out by computer simulation based on a three-dimensional structure of the target protein. Therefore, the structural analysis of the target protein is highly important.

X-ray crystallography has been carried out for structure analyses of the GPCRs, and the X-ray crystal structure of bacteriorhodopsin was clarified in the 1990s (NPL 1), and in 2000, structural analysis for bovine rhodopsin was carried out for the first time as a mammalian GPCR (NPL 2). Thereafter, in 2007, the structural analysis for a $\beta_2$-adrenergic receptor was carried out for the first time as a human GPCR (NPL 3).

In the GPCRs that have been structure-determined so far, those that have been succeeded in the structural analysis in the wild-type state can be prepared in a large amount, and other GPCRs are not expressed in tissues at a level enough to be purified, and even in a case of forced expression in cultured cells, from the viewpoint of stability and expression level, there is a problem that it is difficult to prepare a large amount of the wild type protein to a level at which it can be crystallized.

The GPCR is commonly composed of seven transmembrane helices and an eighth amphipathic helix. The helix is connected by six loops, with a N-terminus and three loops existing outside the cell and the C-terminus and three loops existing inside the cell. Since a transmembrane part of GPCR is a part that transmits extracellular agonist binding signal into the cell, it is inherently highly flexible and causes GPCR to become unstable during purification. In addition, since GPCR has great diversity in the structure of a ligand binding site centering on an extracellular loop region, it is not easy to predict a three-dimensional structure in different receptor families.

With regard to the structure analysis of GPCR, various studies have been conducted so far in order to improve stability, expression level, crystallinity, and the like, and the structural analysis of about 40 types of human GPCRs has been performed. For example, there are reported examples of successful structural analysis by using a technique of replacing a GPCR intracellular third loop involved in the interaction between GPCR and a G protein with T4 Lysozyme (hereinafter, referred to as T4L) (NPL 3 and PTL 1) or with Cytochrome b562RIL (NPL 4 and PTL 1).

In addition, a technique has been reported for stabilizing the GPCR structure into any three-dimensional structure by introducing a mutation into amino acid sequences of GPCR (NPL 5). This technique is effective in that the structure can be fixed to be an agonist-binding type or an antagonist-binding type depending on the introduction site of the mutation.

A technique of forming a complex of an antibody that specifically recognizes GPCR and GPCR (NPL 6) is a technique in which an antibody fragment specific for a specific GPCR stabilizes the specific GPCR. In addition, when crystallization is performed, the antibody fragment binds to GPCR to expand an extra-membrane hydrophilic surface that can contribute to intermolecular contact in a crystal lattice, thereby promoting crystal formation.

CITATION LIST

Patent Literature

PTL 1: United States Patent Application, Publication No. 2012/0288913

Non-Patent Literature

NPL 1: Pebay-Peyroula E et al. Science, 1997; 277:1676-81
NPL 2: Palczewski K et al. Science, 2000; 289(5480):739-45
NPL 3: Rosenbaum et al. Science 2007; 318:1266-73
NPL 4: Chun et al. Structure 2012; 20: 967-976
NPL 5: Serrano et al. Proc. Natl. Acad. Sci. USA, 2008; 105: 877-882
NPL 6: Hino et al. Nature, 2012; 482: 237-240

SUMMARY OF INVENTION

Technical Problem

As described above, the structural analysis of a target protein in drug discovery is highly important, and various studies have been conducted so far regarding the structural analysis of GPCRs that have problems in stability and the like. However, a technique disclosed in NPL 5 specifies mutation introduction sites of other GPCR based on the effective mutation introduction sites of an adenosine A2a receptor, and thus is not highly versatile. Further, it takes a lot of labor and time to search for combinations of mutation introduction sites and to perform structural analysis. The technique disclosed in NPL 6 requires the preparation of a specific antibody fragment for each GPCR.

In view of the above circumstances, an object of the present invention is to provide a method of enabling efficient structural analysis of a target protein that has been impossible or difficult to analyze so far, by stabilizing the target protein. Another object of the present invention is to provide a general-purpose antibody that stabilizes the protein efficiently and effectively in the structural analysis of the target protein or an antigen-binding fragment thereof.

Solution to Problem

The inventors of the present invention have prepared a BRIL fusion protein in which a membrane protein is fused to BRIL as a tag protein when stabilizing the target membrane protein, and have found that the BRIL fusion protein can be stabilized by using an antibody which binds to BRIL or an antigen-binding fragment thereof. With this, the present invention has completed.

That is, the present invention relates to the following <1> to <27>.

<1> A method of stabilizing a BRIL fusion protein in which BRIL is fused to a target protein using an antibody which binds to BRIL or an antigen-binding fragment thereof.

<2> The method according to <1>, in which the BRIL fusion protein is a protein in which two adjacent helix structures of the target protein are fused by BRIL.

<3> The method according to <1> or <2>, in which the target protein is a membrane expressed protein.

<4> The method according to <3>, in which the membrane expressed protein is any one selected from a G protein-coupled receptor (GPCR), an ion channel, and a transporter.

<5> The method according to any one of <1> to <4>, comprising: stabilizing the BRIL fusion protein by binding an antibody which binds to BRIL or an antigen-binding fragment thereof to BRIL of the BRIL fusion protein.

<6> The method according to any one of <1> to <5>, in which the antibody which binds to BRIL or the antigen-binding fragment thereof is any one selected from the following (1) to (3):

(1) an antibody which binds to at least any one of a third helix structure and a fourth helix structure of BRIL or an antigen-binding fragment thereof, (2) an antibody which binds to at least a portion of the third helix structure to the fourth helix structure of BRIL or an antigen-binding fragment thereof, (3) an antibody which binds to at least one amino acid residue selected from amino acid residues of $67^{th}$ Ile (I), $71^{st}$ Gln (Q), $74^{th}$ Asp (D), $77^{th}$ Lys (K), $78^{th}$ Leu (L), $83^{rd}$ Lys (K), $85^{th}$ Lys (K), $86^{th}$ Glu (E), $88^{th}$ Gln (Q), $89^{th}$ Ala (A), $90^{th}$ Ala (A), $92^{nd}$ Glu (E), $93^{rd}$ Gln (Q), $96^{th}$ Thr (T), $97^{th}$ Thr (T), $99^{th}$ Asn (N), and $100^{th}$ Ala (A) from a N-terminus of BRIL or an antigen-binding fragment thereof, <7> The method according to any one of <1> to <6>, in which the antibody which binds to BRIL or the antigen-binding fragment thereof is any one selected from the following (i) to (iii):

(i) an antibody which binds by competing with an antibody in which complementarity determining regions (CDRs) 1 to 3 of a heavy chain variable region (VH) of the antibody contain amino acid sequences represented by SEQ ID NOs: 1 to 3, respectively, and in which CDRs 1 to 3 of a light chain variable region (VL) of the antibody contain amino acid sequences represented by SEQ ID NOs: 4 to 6, respectively, or an antigen-binding fragment thereof, (ii) an antibody which binds to an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof, and (iii) an antibody which binds to the same epitope as an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof.

<8> The method according to any one of <1> to <7>, in which in the antibody which binds to BRIL or the antigen-binding fragment thereof, CDRs 1 to 3 of VH of the antibody contain amino acid sequences having homology of 90% or more with the amino acid sequences represented by SEQ ID NOs: 1 to 3, respectively, and CDRs 1 to 3 of VL of the antibody contain amino acid sequences having homology of 90% or more with the amino acid sequences represented by SEQ ID NOs: 4 to 6, respectively.

<9> An anti-BRIL antibody or an antigen-binding fragment thereof, which is any one selected from the following (1) to (3):

(1) an antibody which binds to at least any one of a third helix structure and a fourth helix structure of BRIL or an antigen-binding fragment thereof, (2) an antibody which binds to at least a portion of the third helix structure to the fourth helix structure of BRIL or an antigen-binding fragment thereof, and (3) an antibody which binds to at least one amino acid residue selected from amino acid residues of $67^{th}$ Ile (I), $71^{st}$ Gln (Q), $74^{th}$ Asp (D), $77^{th}$ Lys (K), $78^{th}$ Leu (L), $83^{rd}$ Lys (K), $85^{th}$ Lys (K), $86^{th}$ Glu (E), $88^{th}$ Gln (Q), $89^{th}$ Ala (A), $90^{th}$ Ala (A), $92^{nd}$ Glu (E), $93^{rd}$ Gln (Q), $96^{th}$ Thr (T), $97^{th}$ Thr (T), $99^{th}$ Asn (N), and $100^{th}$ Ala (A) from a N-terminus of BRIL or an antigen-binding fragment thereof, <10> The anti-BRIL antibody or the antigen-binding fragment thereof according to <9>, which is any one selected from the following (i) to (iii):

(i) an antibody which binds by competing with an antibody in which CDRs 1 to 3 of VH of the antibody contain the amino acid sequences represented by SEQ ID NOs: 1 to 3, respectively, and in which CDRs 1 to 3 of a light chain variable region (VL) of the antibody contain the amino acid sequences represented by SEQ ID NOs: 4 to 6, respectively, or an antigen-binding fragment thereof, (ii) an antibody which binds to an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof, and (iii) an antibody which binds to the same epitope as an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof.

<11> The anti-BRIL antibody or the antigen-binding fragment thereof according to <9> or <10>, in which in the antibody which binds to BRIL or the antigen-binding fragment thereof, CDRs 1 to 3 of VH of the antibody contain amino acid sequences having homology of 90% or more with the amino acid sequences represented by SEQ ID NOs: 1 to 3, respectively, and CDRs 1 to 3 of VL of the antibody contain amino acid sequences having homology of 90% or more with the amino acid sequences represented by SEQ ID NOs: 4 to 6, respectively.

<12> A crystal promotion method or a crystal production method of a BRIL fusion protein in which BRIL is fused to a target protein using an antibody which binds to BRIL or an antigen-binding fragment thereof.

<13> The crystal promotion method or the crystal production method according to <12>, in which the BRIL fusion protein is a protein in which two adjacent helix structures of the target protein are fused by BRIL.

<14> The crystal promotion method or the crystal production method according to <12> or <13>, wherein the target protein is a membrane expressed protein.

<15> The crystal promotion method or the crystal production method according to <14>, in which the membrane expressed protein is any one selected from a GPCR, an ion channel, and a transporter.

<16> The crystal promotion method or the crystal production method according to any one of <12> to <15>, comprising: stabilizing the BRIL fusion protein by binding an antibody which binds to BRIL or an antigen-binding fragment thereof to BRIL of the BRIL fusion protein.

<17> The crystal promotion method or the crystal production method according to any one of <12> to <16>, in which the antibody which binds to BRIL or the antigen-binding fragment thereof is any one selected from the following (1) to (3):

(1) an antibody which binds to at least any one of a third helix structure and a fourth helix structure of BRIL or an antigen-binding fragment thereof, (2) an antibody which binds to at least a portion of the third helix structure to the fourth helix structure of BRIL or an antigen-binding fragment thereof, and (3) an antibody which binds to at least one amino acid residue selected from amino acid residues of $67^{th}$ Ile (I), $71^{st}$ Gln (Q), $74^{th}$ Asp (D), $77^{th}$ Lys (K), $78^{th}$ Leu (L), $83^{rd}$ Lys (K), $85^{th}$ Lys (K), $86^{th}$ Glu (E), $88^{th}$ Gln (Q), $89^{th}$ Ala (A), $90^{th}$ Ala (A), $92^{nd}$ Glu (E), $93^{rd}$ Gln (Q), $96^{th}$ Thr (T), $97^{th}$ Thr (T), $99^{th}$ Asn (N), and $100^{th}$ Ala (A) from a N-terminus of BRIL or an antigen-binding fragment thereof.

<18> The crystal promotion method or the crystal production method according to any one of <12> to <17>, in which the antibody which binds to BRIL or the antigen-binding fragment thereof is any one selected from the following (i) to (iii):

(i) an antibody which binds by competing with an antibody in which CDRs 1 to 3 of VH of the antibody contain the amino acid sequences represented by SEQ ID NOs: 1 to 3, respectively, and in which CDRs 1 to 3 of a light chain variable region (VL) of the antibody contain the amino acid sequences represented by SEQ ID NOs: 4 to 6, respectively, or an antigen-binding fragment thereof, (ii) an antibody which binds to an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof, and (iii) an antibody which binds to the same epitope as an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof.

<19> The crystal promotion method or the crystal production method according to any one of <12> to <18>, in which in the antibody which binds to BRIL or the antigen-binding fragment thereof, CDRs 1 to 3 of VH of the antibody contain amino acid sequences having homology of 90% or more with the amino acid sequences represented by SEQ ID NOs: 1 to 3, respectively, and CDRs 1 to 3 of VL of the antibody contain amino acid sequences having homology of 90% or more with the amino acid sequences represented by SEQ ID NOs: 4 to 6, respectively.

<20> A method of analyzing a three-dimensional structure of a BRIL fusion protein in which BRIL is fused to a target protein using an antibody which binds to BRIL or an antigen-binding fragment thereof.

<21> The method of analyzing a three-dimensional structure according to <20>, in which the BRIL fusion protein is a protein in which two adjacent helix structures of the target protein are fused by BRIL.

<22> The method of analyzing a three-dimensional structure according to <20> or <21>, in which the target protein is a membrane expressed protein.

<23> The method of analyzing a three-dimensional structure according to <22>, in which the membrane expressed protein is any one selected from a GPCR, an ion channel, and a transporter.

<24> The method of analyzing a three-dimensional structure according to any one of <20> to <23>, stabilizing the BRIL fusion protein by binding an antibody which binds to BRIL or an antigen-binding fragment thereof to BRIL of the BRIL fusion protein.

<25> The method of analyzing a three-dimensional structure according to any one of <20> to <24>, in which the antibody which binds to BRIL or the antigen-binding fragment thereof is any one selected from the following (1) to (3):

(1) an antibody which binds to at least any one of a third helix structure and a fourth helix structure of BRIL or an antigen-binding fragment thereof, (2) an antibody which binds to at least a portion of the third helix structure to the fourth helix structure of BRIL or an antigen-binding fragment thereof, and (3) an antibody which binds to at least one amino acid residue selected from amino acid residues of $67^{th}$ Ile (I), $71^{st}$ Gln (Q), $74^{th}$ Asp (D), $77^{th}$ Lys (K), $78^{th}$ Leu (L), $83^{rd}$ Lys (K), $85^{th}$ Lys (K), $86^{th}$ Glu (E), $88^{th}$ Gln (Q), $89^{th}$ Ala (A), $90^{th}$ Ala (A), $92^{nd}$ Glu (E), $93^{rd}$ Gln (Q), $96^{th}$ Thr (T), $97^{th}$ Thr (T), $99^{th}$ Asn (N), and $100^{th}$ Ala (A) from a N-terminus of BRIL or an antigen-binding fragment thereof.

<26> The method of analyzing a three-dimensional structure according to any one of <20> to <25>, in which the antibody which binds to BRIL or the antigen-binding fragment thereof is any one selected from the following (i) to (iii):

(i) an antibody which binds by competing with an antibody in which complementarity determining regions (CDRs) 1 to 3 of a heavy chain variable region (VH) of the antibody contain amino acid sequences represented by SEQ ID NOs: 1 to 3, respectively, and in which CDRs 1 to 3 of a light chain variable region (VL) of the antibody contain amino acid sequences represented by SEQ ID NOs: 4 to 6, respectively, or an antigen-binding fragment thereof, (ii) an antibody which binds to an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof, and (iii) an antibody which binds to the same epitope as an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof.

<27> The method of analyzing a three-dimensional structure according to any one of <20> to <26>, in which in the antibody which binds to BRIL or the antigen-binding fragment thereof, CDRs 1 to 3 of VH of the antibody contain amino acid sequences having homology of 90% or more with the amino acid sequences represented by SEQ ID NOs: 1 to 3, respectively, and CDRs 1 to 3 of VL of the antibody contain amino acid sequences having homology of 90% or more with the amino acid sequences represented by SEQ ID NOs: 4 to 6, respectively.

Advantageous Effects of Invention

According to this invention, it is possible to provide a method of enabling efficient structural analysis of a target protein that has been impossible or difficult to analyze so far. It is possible to provide a method of stabilizing the protein efficiently and effectively in the structural analysis of the target protein. According to the present invention, it is possible to provide an antibody useful for stabilizing the protein, a nucleic acid encoding the antibody, a vector containing the nucleic acid, an antibody producing cell containing the vector, a method of producing the antibody, and a method of using the antibody in a protein structural analysis.

BRIEF DESCRIPTION OF DRAWINGS

In FIG. 1, a horizontal axis represents a protein elution time (minutes), and a vertical axis represents a specific fluorescence intensity (RFU).

DESCRIPTION OF EMBODIMENTS

Figure 1:
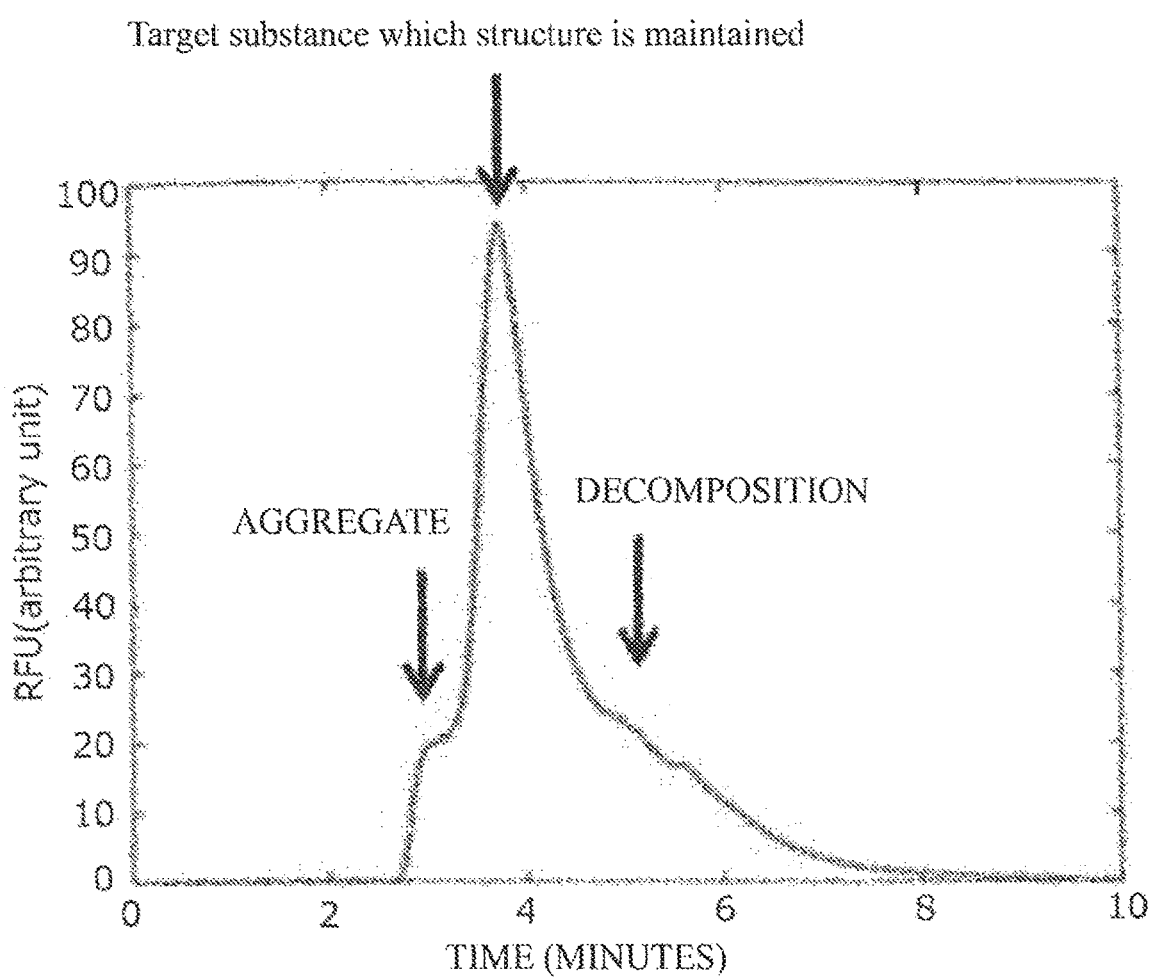
FIG. 1 is a graph illustrating a result of a histogram obtained by fluorescence size exclusion chromatography (FSEC) of hChemR23-BRIL fusion protein.

The present invention relates to a method of stabilizing a BRIL fusion protein (hereinafter, also abbreviated as a stabilization method of the present invention) using an antibody which binds to BRIL (hereinafter, also abbreviated as an anti-BRIL antibody) or an antigen-binding fragment thereof. In the stabilization method of the present invention, in performing structural analysis of a target protein, a BRIL fusion protein in which the target protein and BRIL are fused is produced in advance, and an antibody which binds to a BRIL part of the BRIL fusion protein or an antigen-binding fragment thereof is allowed to coexist with and bind to the BRIL fusion protein, so that the BRIL fusion protein can be stabilized.

In addition, the present invention also includes a method of purifying BRIL fusion protein, a preparation method, a crystallization method, a promotion method of crystallization, a crystal production method, and a three-dimensional structural analysis method of BRIL-fusion protein by allowing the BRIL fusion protein to exist stably.

As an anti-BRIL antibody or an antigen-binding fragment thereof used in the stabilization method of the present invention, any of anti-BRIL antibodies or antigen-binding fragments thereof described later can be used. As a method of purifying the BRIL fusion protein of the present invention, a method of efficiently and specifically purifying the BRIL fusion protein by immobilizing the anti-BRIL antibody or the antigen-binding fragment thereof on a column or bead and binding it to the BRIL fusion protein is exemplified.

According to the stabilization method of the present invention, since the BRIL fusion protein can exist stably in a solution, the stabilization method of the present invention can be used for negative stain electron microscopy and cryo electron microscope analysis of the target protein. In this case, since the anti-BRIL antibody or the antigen-binding fragment thereof can be used as a marker that gives directionality to the target BRIL fusion protein in a soluble state, it can be used for analysis of an electron microscope analysis image of the target protein.

That is, when the anti-BRIL antibody or the antigen-binding fragment thereof of the present invention is bound to the BRIL fusion protein in a solution, the antibody or the antigen-binding fragment thereof bound to the BRIL part of the target BRIL fusion protein can be recognized as a marker for distinguishing a BRIL part and a target protein part in a three-dimensional structure, and thus it is useful for structural analysis of the target protein.

Further, according to the stabilization method of the present invention, the BRIL fusion protein can be regularly arranged by binding the anti-BRIL antibody or the antigen-binding fragment thereof to the BRIL part of the BRIL fusion protein in the process of producing crystals, and thereby the crystallization of the target protein can be efficiently promoted. The stabilization method of the present invention is also useful as a method of efficiently promoting crystallization of a target protein, which has heretofore been impossible or difficult to crystallize.

According to the crystal production method of the present invention, the BRIL fusion protein and the anti-BRIL antibody or the antigen-binding fragment thereof are mixed at an appropriate molar ratio, and then mixed with polyethylene glycol (PEG), a salt, an organic solvent, and a buffer so as to produce a co-crystal of the target BRIL fusion protein and the anti-BRIL antibody or the antigen-binding fragment thereof.

Examples of the crystal production method of the present invention includes a step of expressing/purifying a BRIL fusion protein, a step of reacting the BRIL fusion protein with an anti-BRIL antibody or an antigen-binding fragment thereof, and a step of co-crystallizing the BRIL fusion protein and the anti-BRIL antibody or the antigen-binding fragment thereof.

As the three-dimensional structural analysis method of the present invention, a three-dimensional structural analysis method including a step of expressing/purifying a BRIL fusion protein, a step of reacting the BRIL fusion protein with an anti-BRIL antibody or an antigen-binding fragment thereof, a step of co-crystallizing the BRIL fusion protein and the anti-BRIL antibody or the antigen-binding fragment thereof, and a step of obtaining X-ray diffraction data; and a three-dimensional structural analysis method including a step of expressing/purifying a BRIL fusion protein, a step of reacting the BRIL fusion protein with an anti-BRIL antibody or an antigen-binding fragment thereof, and a step of structural analysis by electron microscope are exemplified.

In addition, the present invention also relates to an anti-BRIL antibody which binds to the BRIL fusion protein or an antigen-binding fragment thereof. The anti-BRIL antibody or the antigen-binding fragment thereof of the present invention can stabilize the BRIL fusion protein by binding to the BRIL part of the BRIL fusion protein.

In the present invention, the BRIL refers to a heat resistant apocytochrome b562 modified protein (also referred to as cytochrome b562RIL) [Chu et al, J. Mol. Biol. (2002) 323, 253-262] (Protein Data Bank ID: PDB 1M6T) in which amino acid residue substitutions of M7W, H102I, and R106L are introduced into the amino acid sequence of apocytochrome b562.

In the present invention, the amino acid residue substitution is indicated in the order of an original amino acid residue, a position of the amino acid residue, and the amino acid residue after substitution.

In addition, BRIL in the present invention is preferably a protein consisting of an amino acid sequence having homology of 90% or more, 91% or more, 92% or more, 93% or more, and 94% or more in this order with the amino acid sequence of SEQ ID NO: 9, or preferably a protein consisting of an amino acid sequence having homology of 95% or more, 96% or more, 97% or more, 98% or more, and 99% or more, and includes a protein constituting a three-dimensional structure consisting of the amino acid sequence of cytochrome b562.

In the present invention, the BRIL fusion protein includes any BRIL fusion protein as long as it is a protein in which BRIL is fused to the target protein. The BRIL fusion protein is preferably fused to the target protein so that BRIL forms at least part of a helix structure of the target protein, and is more preferably fused to the target protein so that BRIL forms at least a part of a loop structure in the structure of the target protein.

The BRIL to be fused to the target protein may be a fragment of BRIL as long as the anti-BRIL antibody or the antigen-binding fragment thereof can bind to the BRIL part in the BRIL fusion protein. The BRIL fragment can be appropriately adjusted in accordance with the kinds of target proteins.

Specifically, examples of the BRIL fusion protein include a BRIL fusion protein which is fused so as to constitute at least a part of an extracellular loop structure, an intracellular loop structure, a vesicular membrane loop structure, or a intravesicular loop structure of the target protein.

More specifically, examples of the BRIL fusion protein in the present invention include a BRIL fusion protein in which all or a part of the loop structure existing between two helix structures existing in the structure of the target protein is replaced or fused with the BRIL protein or the fragment.

The two helix structures existing in the structure of the target protein may or may not be adjacent to each other on the primary sequence of the protein, and the two helix structures constituting the target protein are preferably adjacent to each other on the three-dimensional structure, and are more preferably adjacent to each other on both of the primary sequence and the three-dimensional structure.

Among a first helix structure and a second helix structure constituting the two adjacent helix structures, a distance between an amino acid residue on the C-terminus side of the first helix structure and an amino acid residue on the N-terminus side or C-terminus side of the second helix structure is preferably short, and the distance is more preferably 10 to 15 angstrom, 11 to 15 angstrom, 10 to 14 angstrom, 11 to 14 angstrom, 11 to 13 angstrom, and 12 to 14 angstrom in the following order.

Examples of the loop structure in the structure of the target protein include a structure directly under a helix structure that penetrates a membrane structure such as each cell membrane and a vesicle membrane of organelle. The BRIL fusion protein can be expressed and purified by substituting or fusing the BRIL protein and the fragment into a part of the loop structure.

Specifically, for example, in a case where BRIL is fused to the intracellular loop of GPCR, from the previously reported GPCR crystallography results, a stable GPCR-BRIL fusion protein can be produced by fusing BRIL to a portion where the $16^{th}$ to $24^{th}$ amino acid regions counted from proline stored in the $5^{th}$ transmembrane helix from the N-terminus of GPCR and the $-24^{th}$ to $-28^{th}$ amino acid regions counted from the proline stored in the $6^{th}$ transmembrane helix overlap (Eugene Chun et al. Structure, 2012; 20: 967-976).

Further, for example, in a case where BRIL is fused to the intracellular loop of a transporter, in the helix structure constituting the transmembrane domain of the transporter protein, the distance between the C-terminus part and the N-terminus part of two adjacent helix structures is measured, and BRIL or the fragment thereof is fused to a part at a distance of about 12 to 14 angstrom so as to produce the BRIL fusion protein.

The target protein used in the present invention may be any protein as long as it can be substituted or fused with BRIL or the fragment thereof, and preferably includes a membrane expressed protein (also referred to as a membrane protein). Examples of membrane proteins include a receptor, an ion channel, a transporter, an enzyme, and a structural protein, and more preferable examples include a receptor, an ion channel, and a transporter.

Examples of the receptor include GPCR.

Examples of the ion channel include CatSper1, CatSper2, CatSper3, CatSper4, TPC1, TPC2, CNGA1, CNGA2, CNGA3, CNGA4, CNGB1, CNGB3, HCN1, HCN2, HCN3, HCN4, KCa1.1, KCa2.1, KCa2.2, KCa2.3, KCa3.1, KNa1.1, KNa1.2, KCa5.1, Kir1.1, Kir2.1, Kir2.2, Kir2.3, Kir2.4, Kir3.1, Kir3.2, Kir3.3, Kir3.4, Kir4.1, Kir4.2, Kir5.1, Kir6.1, Kir6.2, Kir7.1, K2P1.1, K2P2.1, K2P3.1, K2P4.1, K2P5.1, K2P6.1, K2P7.1, K2P9.1, K2P10.1, K2P12.1, K2P13.1, K2P15.1, K2P16.1, K2P17.1, K2P18.1, Kv1.1, Kv1.2, Kv1.3, Kv1.4, Kv1.5, Kv1.6, Kv1.7, Kv1.8, Kv2.1, Kv2.2, Kv3.1, Kv3.2, Kv3.4, Kv4.1, Kv4.2, Kv4.3, Kv5.1, Kv6.1, Kv6.2, Kv6.3, Kv6.4, Kv7.1, Kv7.2, Kv7.3, Kv7.4, Kv7.5, Kv8.1, Kv8.2, Kv9.1, Kv9.2, Kv9.3, Kv10.1, Kv10.2, Kv11.1, Kv11.2, Kv11.3, Kv12.1, Kv12.2, Kv12.3, RyR1, RyR2, RyR3, TRPA1, TRPC1, TRPC2, TRPC3, TRPC4, TRPC5, TRPC6, TRPC7, TRPM1, TRPM2, TRPM3, TRPM4, TRPM5, TRPM6, TRPM7, TRPM8, TRPML1, TRPML2, TRPML3, TRPP1, TRPP2, TRPP3, TRPV1, TRPV2, TRPV3, TRPV4, TRPV5, TRPV6, Cav1.1, Cav1.2, Cav1.3, Cav1.4, Cav2.1, Cav2.2, Cav2.3, Cav3.1, Cav3.2, Cav3.3, Hv1, Nav1.1, Nav1.2, Nav1.3, Nav1.4, Nav1.5, Nav1.56, Nav1.7, Nav1.8, Nav1.9, 5-HT3AB, 5-HT3A, 5-HT3B, 5-HT3C, 5-HT3D, 5-HT3E, ASIC1, ASIC2, ASIC3, ENaCαβγ, ENaC α, ENaC β, ENaC δ, ENaC γ, GABAA receptor α1 subunit, GABAA receptor α2 subunit, GABAA receptor α3 subunit, GABAA receptor α4 subunit, GABAA receptor α5 subunit, GABAA receptor α6 subunit, GABAA receptor β1 subunit, GABAA receptor β2 subunit, GABAA receptor β3 subunit, GABAA receptor γ1 subunit, GABAA receptor γ2 subunit, GABAA receptor γ3 subunit, GABAA receptor δ subunit, GABAA receptor ε subunit, GABAA receptor θ subunit, GABAA receptor π subunit, GABAA receptor ρ1 subunit, GABAA receptor ρ2 subunit, GABAA receptor ρ3 subunit, glycine receptor α1 subunit, glycine receptor α2 subunit, glycine receptor α3 subunit, glycine receptor α4 subunit, glycine receptor β subunit, GluA1, GluA2, GluA3, GluA4, GluD1, GluD2, GluK1, GluK2, GluK3, GluK4, GluK5, GluN1, GluN2A, GluN2B, GluN2C, GluN2D, GluN3A, GluN3B, IP3R1, IP3R2, IP3R3, nicotinic acetylcholine receptor α1 subunit, nicotinic acetylcholine receptor α2 subunit, nicotinic acetylcholine receptor α3 subunit, nicotinic acetylcholine receptor α4 subunit, nicotinic acetylcholine receptor α5 subunit, nicotinic acetylcholine receptor α6 subunit, nicotinic acetylcholine receptor α7 subunit, nicotinic acetylcholine receptor α8 subunit, nicotinic acetylcholine receptor α9 subunit, nicotinic acetylcholine receptor α10 subunit, nicotinic acetylcholine receptor β1 subunit, nicotinic acetylcholine receptor β2 subunit, nicotinic acetylcholine receptor β3 subunit, nicotinic acetylcholine receptor β4 subunit, nicotinic acetylcholine receptor γ subunit, nicotinic acetylcholine receptor δ subunit, nicotinic acetylcholine receptor ε subunit, P2X1, P2X2, P2X3, P2X4, P2X5, P2X6, P2X7, ZAC, AQP0, AQP1, AQP2, AQP3, AQP4, AQP5, AQP6, AQP7, AQP8, AQP9, AQP10, C1C-1, C1C-2, C1C-3, C1C-4, C1C-5, C1C-6, C1C-7, C1C-Ka, C1C-Kb, CFTR, CaCC, Maxi Cl-, VRAC, Cx23, Cx25, Cx26, Cx30, Cx30.2, Cx30.3, Cx31, Cx31.1, Cx31.9, Cx32, Cx36, Cx37, Cx40, Cx40.1, Cx43, Cx45, Cx46, Cx47, Cx50, Cx59, Cx62, Px1, Px2, Px3, Navi2.1, and the like.

Examples of the GPCR include 5-HT1A, 5-HT1B, 5-HT1D, 5-ht1e, 5-HT1F, 5-HT2A, 5-HT2B, 5-HT2C, 5-HT4, 5-HT5a, 5-HT6, 5-HT7, M1, M2, M3, M4, M5, A1, A2A, A2B, A3, α1A-adrenoceptor, α1B-adrenoceptor, α1D-adrenoceptor, α2A-adrenoceptor, α2B-adrenoceptor, α2C-adrenoceptor, β1-adrenoceptor, β2-adrenoceptor, β3-adrenoceptor, C3a, C5a, C5L2, AT1, AT2, APJ, GPBA, BB1, BB2, BB3, B1, B2, CB1, CB2, CCR1, CCR2, CCR3, CCR4, CCR5, CCR6, CCR7, CCR8, CCR9, CCR10, CXCR1, CXCR2, CXCR3, CXCR4, CXCR5, CXCR6, CXCR7, CX3CR1, XCR1, CCK1, CCK2, D1, D2, D3, D4, D5, ETA, ETB, GPER, FPR1, FPR2/ALX, FPR3, FFA1, FFA2, FFA3, GPR42, GAL1, GAL2, GAL3, ghrelin, FSH, LH, TSH, GnRH, GnRH2, H1, H2, H3, H4, HCA1, HCA2, HCA3, kisspeptin, BLT1, BLT2, CysLT1, CysLT2, OXE, FPR2/ALX, LPA1, LPA2, LPA3, LPA4, LPA5, S1P1, S1P2, S1P3, S1P4, S1P5, MCH1, MCH2, MC1, MC2, MC3, MC4, MC5, MT1, MT2, motilin, NMU1, NMU2, NPFF1, NPFF2, NPS, NPBW1, NPBW2, Y1, Y2, Y4, Y5, NTS1, NTS2, δ, κ, μ, NOP, OX1, OX2, P2Y1, P2Y2, P2Y4, P2Y6, P2Y11, P2Y12, P2Y13, P2Y14, QRFP, PAF, PKR1, PKR2, PRRP, DP1, DP2, EP1, EP2, EP3, EP4, FP, IP1, TP, PAR1, PAR2, PAR3, PAR4, RXFP1, RXFP2, RXFP3, RXFP4, sst1, sst2, sst3, sst4, sst5, NK1, NK2, NK3, TRH1, TA1, UT, V1A, V1B, V2, OT, CCRL2, CMKLR1, GPR1, GPR3, GPR4, GPR6, GPR12, GPR15, GPR17, GPR18, GPR19, GPR20, GPR21, GPR22, GPR25, GPR26, GPR27, GPR31, GPR32, GPR33, GPR34, GPR35, GPR37, GPR37L1, GPR39, GPR42, GPR45, GPR50, GPR52, GPR55, GPR61, GPR62, GPR63, GPR65, GPR68, GPR75, GPR78, GPR79, GPR82, GPR83, GPR84, GPR85, GPR87, GPR88, GPR101, GPR119, GPR120, GPR132, GPR135, GPR139, GPR141, GPR142, GPR146, GPR148, GPR149, GPR150, GPR151, GPR152, GPR153, GPR160, GPR161, GPR162, GPR171, GPR173, GPR174, GPR176, GPR182, GPR183, LGR4, LGR5, LGR6, LPAR6, MAS1, MAS1L, MRGPRD, MRGPRE, MRGPRF, MRGPRG, MRGPRX1, MRGPRX2, MRGPRX3, MRGPRX4, OPN3, OPN5, OXGR1, P2RY8, P2RY10, SUCNR1, TAAR2, TAAR3, TAAR4, TAAR5, TAAR6, TAAR8, TAAR9, CCPB2, CCRL1, FY, CT, calcitonin receptor-like, CRF1, CRF2, GHRH, GIP, GLP-1, GLP-2, glucagon, secretin, PTH1, PTH2, PAC1, VPAC1, VPAC2, BAI1, BAI2, BAI3, CD97, CELSR1, CELSR2, CELSR3, ELTD1, EMR1, EMR2, EMR3, EMR4P, GPR56, GPR64, GPR97, GPR98, GPR110, GPR111, GPR112, GPR113, GPR114, GPR115, GPR116, GPR123, GPR124, GPR125, GPR126, GPR128, GPR133, GPR143, GPR144, GPR157, LPHN1, LPHN2, LPHN3, CaS, GPRC6, GABAB1, GABAB2, mGlu1, mGlu2, mGlu3, mGlu4, mGlu5, mGlu6, mGlu7, mGlu8, GPR156, GPR158, GPR179, GPRC5A, GPRC5B, GPRC5C, GPRC5D, frizzled, FZD1, FZD2, FZD3, FZD4, FZD5, FZD6, FZD7, FZD8, FZD9, FZD10, SMO, and the like.

Examples of the transporter include ABC1, ABC2, ABC3, ABCR, ABCA5, ABCA6, ABCA7, ABCA8, ABCA9, ABCA10, ABCA12, ABCA13, ABCB1, ABCB2, ABCB3, ABCB4, ABCB5, ABCB6, ABCB7, ABCB8, ABCB9, ABCB10, ABCB11, ABCC1, ABCC2, ABCC3, ABCC4, ABCC5, ABCC6, ABCC7, ABCC8, ABCC9, ABCC10, ABCC11, ABCC12, ABCD1, ABCD2, ABCD3, ABCG1, ABCG2, ABCG4, ABCG5, ABCG8, F-type ATPase α subunit, F-type ATPase β subunit, F-type ATPase γ subunit, F-type ATPase δ subunit, F-type ATPase ε subunit, F-type ATPase A subunit, F-type ATPase B subunit, F-type ATPase C subunit, F-type ATPase D subunit, F-type ATPase E subunit, F-type ATPase F2 subunit, F-type ATPase F6 subunit, F-type ATPase G2 subunit, F-type ATPase 8 subunit, V-type ATPase V1 motor A subunit, V-type ATPase V1 motor B1 subunit, V-type ATPase V1 motor B2 subunit, V-type ATPase V1 motor C1 subunit, V-type ATPase V1 motor D subunit, V-type ATPase V1 motor E1 subunit, V-type ATPase V1 motor E2 subunit, V-type ATPase V1 motor F subunit, V-type ATPase V1 motor G1 subunit, V-type ATPase V1 motor G2 subunit, V-type ATPase V1 motor G3 subunit, V-type ATPase V1 motor H subunit, V-type ATPase V0 motor a1 subunit V-type ATPase V0 motor a2 subunit, V-type ATPase V0 motor a3 subunit, V-type ATPase V0 motor a4 subunit, V-type ATPase V0 motor b subunit, V-type ATPase V0 motor c subunit, V-type ATPase V0 motor d1 subunit, V-type ATPase V0 motor d2 subunit, V-type ATPase V0 motor e1 subunit, V-type ATPase V0 motor e2 subunit, sodium/potassium-transporting ATPase subunit α-1, sodium/potassium-transporting ATPase subunit α-2, sodium/potassium-transporting ATPase subunit α-3, sodium/potassium-transporting ATPase subunit α-4, sodium/potassium-transporting ATPase subunit β-1, sodium/potassium-transporting ATPase subunit β-2, sodium/potassium-transporting ATPase subunit β-3, sodium/potassium-transporting ATPase subunit γ, SERCA1, SERCA2, SERCA3, PMCA1, PMCA2, PMCA3, PMCA4, SPCA1, SPCA2, ATP4A, ATP12A, ATP4B, ATP7A, ATP7B, ATP8A1, ATP8A2, ATP8B1, ATP8B2, ATP8B3, ATP8B4, ATP9A, ATP9B, ATP10A, ATP10B, ATP10D, ATP11A, ATP11B, ATP11C, synaptic vesicle glycoprotein 2A, EAAT1, EAAT12, EAAT3, EAAT4, EAAT5, ASCT1, ASCT2, GLUT1, GLUT2, GLUT3, GLUT4, GLUT5, GLUT6, GLUT7, GLUT8, GLUT9, GLUT10, GLUT11, GLUT12, HMIT, rBAT, 4F2hc, CAT1, CAT2, CAT3, CAT4, Probable cationic amino acid transporter, LAT1, LAT2, y+LAT1, y+LAT2, b0, +AT, Asc-1, xCT, AGT1, AE1, AE2, AE3, AE4, NBCe1, NBCe2, NBCn1, NBCn2, NDCBE, BTR1, SGLT1, SGLT2, SGLT3, SGLT4, SGLT5, CHT, NIS, SMVT, SMCT1, SMCT2, SMIT1, SMIT2, NET, DAT, GAT1, GAT2, GAT3, BGT1, TauT, CT1, GlyT1, GlyT2, ATB0, PROT, B0AT1, B0AT2, B0AT3, NTT4, NTT5, SIT1, NCX1, NCX2, NCX3, NHE1, NHE2, NHE3, NHE4, NHE5, NHE6, NHE7, NHE8, NHE9, NHA1, NHA2, Sperm-NHE, NHE11, NTCP, ASBT, P3, P4, P5, SOAT, P7, NRAMP1, DMT1, NKCC2, NKCC1, NCC, KCC1, KCC2, KCC3, KCC4, CCC9, CCC6, NaS1, NaS2, NaC1, NaC2, NaC3, UT-A, UT-B, PepT1, PepT2, PHT1, PHT2, MCT1, V MCT2, MCT3, MCT4, MCT5, MCT6, MCT7, MCT8, MCT9, MCT11, MCT12, MCT13, MCT14, TAT1, NPT1, NPT3, NPT4, Sodium/phosphate cotransporter homolog, AST, VGLUT1, VGLUT2, VGLUT3, VNUT, VMAT1, VMAT2, VAChT, solute carrier family 18 member B1, FOLT, ThTr1, ThTr2, PiT1, PiT2, OCT1, OCT2, OCT3, OCTN1, OCTN2, CT2, OAT1, OAT2, OAT3, OAT4, OAT5, Organic anion transporter 4, URAT1, ORCTL3, ORCTL4, FLIPT1, BOIT, ORCTL2, OAT6, SLC22A23, SLC22A24, UST6, solute carrier family 22 member 31, and the like.

Moreover, examples of the transporter include SVCT1, SVCT2, SVCT3, SNBT1, NKCX1, NKCX2, NKCX3, NKCX4, NKCX5, NKCX6, CIC, DIC, OGC, ODC, SLC25A34, SLC25A35, solute carrier family 25 member 47, solute carrier family 25 member 48, AGC1, AGC2, GC1, GC2, ORC1, ORC2, CAC, ORNT3, SLC25A38, CGI-69, MCFP, SLC25A44, SLC25A45, PHC, ANT1, ANT2, ANT3, ANT4, GDC, PMP34, DNC, SAMC1, SLC25A42, APC1, APC2, APC3, MFTC, PNC1, PNC2, SCaMC-3L, SLC25A43, UCP1, UCP2, UCP3, UCP4, UCP5, KMCP1, mitochondrial carrier 1, mitochondrial carrier 2, solute carrier family 25 member 51, solute carrier family 25 member 52, solute carrier family 25 member 53, Mitoferrin1, Mitoferrin2, SLC25A46, Sat-1, DTDST, DRA, Pendrin, PAT-1, SLC26A7, SLC26A9, Prestin, Tat1, SLC26A10, KBAT, FATP1, FATP2, FATP3, FATP4, FATP5, FATP6, CNT1, CNT2, CNT3, ENT1, ENT2, ENT3, PMAT, ZnT1, ZnT2, ZnT3, ZnT4, ZnT5, ZnT6, ZnT7, ZnT8, ZnT9, ZnT10, CTR1, CTR2, VIAAT, ACATN1, NaPi-IIa, NaPi-IIb, NaPi-IIc, CMP-sialic acid transporter, UDP-galactose transporter, UDP-N-acetylglucosamine transporter, MGC2541, FLJ11130, UGTREL1, PAPS transporter 1, PAPS transporter 2, YEA, GDP-Fucose transporter, OVCOV1, UDP-glucuronic acid/UDP-N-acetylgalactosamine dual transporter, HFRC1, FRCL1, solute carrier family 35 member E1, solute carrier family 35 member E2, solute carrier family 35 member E2B, solute carrier family 35 member E3, solute carrier family 35 member E4, solute carrier family 35 member F1, solute carrier family 35 member F2, solute carrier family 35 member F3, solute carrier family 35 member F4, solute carrier family 35 member F5, solute carrier family 35 member F6, solute carrier family 35 member G1, solute carrier family 35 member G2, solute carrier family 35 member G3, solute carrier family 35 member G4, solute carrier family 35 member G5, solute carrier family 35 member G6, PAT1, PAT2, PAT3, PAT4, SPX1, SPX2, SPX3, SPX4, SNAT1, SNAT2, SNAT3, SNAT4, SNAT5, SNAT6, SNAT7, Putative sodium-coupled neutral amino acid transporter 8, Putative sodium-coupled neutral amino acid transporter 9, PP1744, AVT2, ZIP1, ZIP2, ZIP3, ZIP4, ZIP5, ZIP6, ZIP7, ZIP8, ZIP9, ZIP10, ZIP11, ZIP12, ZIP13, ZIP14, IREG1, MgtE, Solute carrier family 41 member 2, Solute carrier family 41 member 3, RhAG, RhBG, RhCG, LAT3, LAT4, EEG1, CTL1, CTL2, CTL3, CTL4, CTL5, Proton-associated sugar transporter A, Membrane-associated transporter protein, Solute carrier family 45 member 3, Solute carrier family 45 member 4, PCFT, TSCOT, SLC46A3, MATE1, MATE2-K, HRG1, FLVCR1, FLVCR2, MFSD7, DIRC2, RAG1AP1, OSTα, OSTβ, RFVT1, RFVT2, RFVT3, OATP1A2, OATP1B1, OATP1B3, OATP1C1, OATP2A1, OATP2B1, OATP3A1, OATP4A1, OATP4C1, OATP5A1, OATP6A1, and the like.

In producing the BRIL fusion protein, a BRIL insertion position in the target protein, lengths of amino acid sequences on the N-terminus and C-terminus of the BRIL fusion protein, and the like can be appropriately adjusted so as to obtain desired monodispersity and stability by performing screening of the BRIL fusion protein such as FSEC described later in examples.

Examples of the antibody or the antigen-binding fragment thereof of the present invention include an antibody which specifically binds to BRIL (anti-BRIL antibody) or an antigen-binding fragment thereof.

An antibody molecule consists of polypeptides called heavy chains (hereinafter, referred to as "H chains") and light chains (hereinafter, referred to as "L chains"). Each H chain is composed of a H chain variable region (also referred to as VH) and a H chain constant region (also referred to as CH) from the N-terminus side, and each L chain is composed of a L chain variable region (also referred to as VL) and a L chain constant region (also referred to as CL) from the N-terminus side.

For CH, $\alpha$, $\delta$, $\varepsilon$, $\gamma$, and $\mu$ chains are known for each subclass. CH is further composed of a CH1 domain, a hinge domain, a CH2 domain and a CH3 domain from the N-terminus side. A domain is a functional structural unit which constitutes a polypeptide of an antibody molecule. The CH2 domain and the CH3 domain are together called a Fc region or simply Fc. For CL, $C_\lambda$ chain and $C_\kappa$ chain are known.

The CH1 domain, the hinge domain, the CH2 domain, the CH3 domain and the Fc region in the invention can be identified by the positions of the amino acid residues from the N-terminus according to the EU index [Kabat et al., Sequences of Proteins of Immunological Interest, US Dept. Health and Human Services (1991)]. Specifically, CH1 is identified as the amino acid sequence of from position 118 to position 215 according to the EU index, and the hinge is identified as the amino acid sequence of from position 216 to position 230 according to the EU index. CH2 is identified as the amino acid sequence of from position 231 to position 340 according to the EU index, and CH3 is identified as the amino acid sequence of from position 341 to position 447 according to the EU index.

Examples of the antibodies of the present invention include particularly, genetically recombinant antibodies such as a recombinant mouse antibody, a recombinant rat antibody, and a recombinant rabbit antibody, chimeric antibodies such as a mouse-type chimeric antibody, a rat chimeric antibody, and a human chimeric antibody (hereinafter, also simply referred to as a chimeric antibody), and recombinant antibodies such as a humanized antibody [also referred to as human complementarity determining region (CDR) implanted antibody], and a human antibody.

The chimeric antibody means, for example, an antibody composed of VH and VL of an antibody of an animal other than human (a non-human animal) and CH and CL of a human antibody. In addition, chimeric antibodies recombined between VH/VL and CH/CL between different animals are also included. As the non-human animal, any animal such as mouse, rat, hamster, and rabbit can be used as long as a hybridoma can be produced.

A hybridoma is a cell which is obtained by cell fusion of a B cell obtained by immunizing a non-human animal with an antigen and a myeloma cell derived from a mouse or the like and which produces a monoclonal antibody having a desired antigen specificity. Therefore, the variable region constituting the antibody produced by the hybridoma consists of the amino acid sequence of a non-human animal antibody.

A human chimeric antibody can be produced by obtaining cDNAs that encode VH and VL of a monoclonal antibody from a hybridoma derived from a non-human animal cell producing the monoclonal antibody, inserting the cDNAs into an expression vector for animal cells having DNA that encodes CH and CL of a human antibody, thereby constructing a human chimeric antibody expression vector, introducing the vector to an animal cell and expressing the antibody.

A humanized antibody is an antibody in which the amino acid sequences of CDRs of VH and VL of an antibody of a non-human animal are implanted to the corresponding CDRs of VH and VL of a human antibody. The region in VH and VL other than the CDRs is called a framework region (referred to as FR below).

A humanized antibody can be produced by constructing cDNA that encodes the amino acid sequence of VH formed from the amino acid sequences of CDRs of VH of an antibody of a non-human animal and the amino acid sequence of FR of VH of any human antibody and cDNA that encodes the amino acid sequence of VL formed from the amino acid sequences of CDRs of VL of an antibody of a non-human animal and the amino acid sequence of FR of VL of any human antibody, inserting the cDNAs to an expression vector for animal cells having DNA that encodes CH and CL of a human antibody, thereby constructing a humanized antibody expression vector, introducing the vector to an animal cell and expressing the antibody.

A human antibody is originally an antibody that naturally exists in the human body, but antibodies obtained from a human antibody phage library and a human antibody-producing transgenic animal and the like which are produced by recent advances in genetic engineering, cell engineering, and developmental engineering technologies are also included.

A human antibody can be obtained by immunizing a mouse having a human immunoglobulin gene (Tomizuka K. et al., Proc Natl Acad Sci USA. 97, 722-7, 2000.) with a desired antigen. A human antibody can be obtained also without immunization by selecting a human antibody having a desired binding activity using a phage display library obtained by amplifying antibody genes from human-derived B cells (Winter G et al., Annu Rev Immunol. 12:433-55. 1994). Moreover, a human antibody can be obtained by producing cells which produce a human antibody having a desired binding activity by immortalizing human B cells using EB virus (Rosen A. et al., Nature 267, 52-54. 1977).

Antibodies existing in the human body can be obtained by, for example, immortalizing lymphocytes isolated from human peripheral blood by infecting EB virus or the like and then cloning to obtain lymphocytes that produce the antibody. The antibody can be purified from the culture in which the lymphocytes are cultured.

A human antibody phage library is a library in which antibody fragments such as Fab and scFv are expressed on the surface of phages by inserting an antibody gene prepared from human B cells to phage genes. It is possible to collect phages on which antibody fragments having a desired antigen binding activity are expressed using binding activity to a substrate to which an antigen is fixed as an index from the library. The antibody fragments can be further converted to a human antibody molecule formed from two whole H chains and two whole L chains using the genetic engineering technique.

A human antibody-producing transgenic animal is an animal in which a human antibody gene is incorporated into the chromosomes of the host animal. Specifically, a human antibody-producing transgenic animal can be produced by introducing a human antibody gene to mouse ES cells, implanting the ES cells to an early embryo of another mouse and then causing development. A human antibody can be produced from a human antibody-producing transgenic animal by culturing a human antibody-producing hybridoma obtained by a general hybridoma production method performed for mammals other than human, producing and accumulating the human antibody in the culture.

As the amino acid sequences of VH and VL of the antibody of the present invention, amino acid sequences of VH and VL of the human antibody, amino acid sequences of VH and VL of the non-human animal antibody, or amino acid sequences of VH and VL of the humanized antibody with CDRs of the non-human animal antibody implanted into any human antibody framework may be used.

The amino acid sequence of CL in the antibody of the present invention may be either an amino acid sequence of a human antibody or an amino acid sequence of a non-human animal antibody, but $C_\kappa$ or $C_\lambda$ of the amino acid sequence of a human antibody is preferable.

The CH of the antibody of the present invention may be any CH as long as it belongs to an immunoglobulin, and preferably, any of subclasses belonging to an IgG class, such as γ1 (IgG1), γ2 (IgG2), γ3 (IgG3), and γ4 (IgG4) can also be used.

As the antibody of the present invention, an Fc fusion protein in which Fc and an antibody fragment are bound, an Fc fusion protein (also referred to as immunoadhesin) in which Fc and a naturally occurring ligand or a receptor are bound, and an Fc fusion protein in which a plurality of Fc regions are fused are included in the present invention. In addition, in order to stabilize the antibody and to control a blood half-life, an Fc region with a modified amino acid residue can also be used in the antibody of the present invention.

The antibody or the antigen-binding fragment thereof of the present invention includes an antibody containing any amino acid residue modified after translation. Examples of the modification after translation include deletion of the lysine residue at the C-terminus of a H chain (lysine clipping), conversion of the glutamine residue at the N-terminus of a polypeptide into pyroglutamine (puroGlu) and the like [Beck et al, Analytical Chemistry, 85, 715-736 (2013)].

Examples of the antigen-binding fragment (also referred to as antibody fragment) in the present invention include Fab, Fab', F(ab')$_2$, scFv, diabody, dsFv, and a peptide containing a plurality of CDRs.

Fab is an antigen-binding fragment which has an antigen binding activity and a molecular weight of approximately fifty thousand and in which about a half of the H chain in the N-terminus side and the entire L chain are linked to each other through disulfide bonds (S—S bonds) (cleaved at the $224^{th}$ amino acid residue in the H chain), of the fragments obtained by treating IgG antibody with a protease, papain.

F(ab')$_2$ is an antigen-binding fragment which has an antigen binding activity and a molecular weight of approximately hundred thousand and which is slightly larger than the one in which Fabs are bound through the S—S bond in the hinge region (cleaved at the $234^{th}$ amino acid residue in the H chain), of the fragments obtained by treating IgG with a protease, pepsin.

Fab' is an antigen-binding fragment which has an antigen binding activity and a molecular weight of approximately fifty thousand and in which the S—S bond in the hinge region of the above F(ab')2 is cleaved.

scFv is a VH-P-VL or VL-P-VH polypeptide in which one VH and one VL are linked using an appropriate peptide linker (P) such as a linker peptide of any number of connected linkers each having four Gly residues and one Ser residue (G4S) and is an antigen-binding fragment having an antigen binding activity.

Diabody is an antigen-binding fragment in which scFvs having same or different antigen binding specificities form a dimer and is an antigen-binding fragment having a divalent antigen binding activity to a same antigen or specific antigen binding activities to different antigens.

dsFv is a fragment in which polypeptides obtained by substituting one amino acid residue in VH and that in VL with cysteine residues are bound through the S—S bond between the cysteine residues.

A peptide containing CDR is composed of and contains at least one or more regions of CDRs of VH or VL. In a peptide containing CDRs, the CDRs can be bound directly or through an appropriate peptide linker.

Production can be performed by constructing DNA that encodes CDRs of VH and VL of the modified antibody of the invention, inserting the DNA into an expression vector for a prokaryote or an expression vector for a eukaryote and introducing the expression vector into a prokaryote or a eukaryote for expression. In addition, a peptide containing CDR can also be produced by a chemical synthesis method such as the Fmoc method or the tBoc method.

Specific examples of the anti-BRIL antibody or the antigen-binding fragment thereof of the present invention include any one selected from the following (a) to (o).

(a) an antibody which binds to a helix structure of BRIL or an antigen-binding fragment thereof, (b) an antibody which binds to any one of first to fourth helix structures of BRIL or an antigen-binding fragment thereof, (c) an antibody which binds to at least any one of the third helix structure and the fourth helix structure of BRIL or an antigen-binding fragment thereof, (d) an antibody which binds to at least a portion of the third helix structure to the fourth helix structure of BRIL or an antigen-binding fragment thereof, (e) an antibody which binds to the third helix structure and the fourth helix structure of BRIL or an antigen-binding fragment thereof, (f) an antibody which binds to at least one amino acid residue selected from the amino acid residues of the $67^{th}$ Ile (I), the $71^{st}$ Gln (Q), the $74^{th}$ Asp (D), the $77^{th}$ Lys (K), the $78^{th}$ Leu (L), the $83^{rd}$ Lys (K), the $85^{th}$ Lys (K), the $86^{th}$ Glu (E), the $88^{th}$ Gln (Q), the $89^{th}$ Ala (A), the $90^{th}$ Ala (A), the $92^{nd}$ Glu (E), the $93^{rd}$ Gln (Q), the $96^{th}$ Thr (T), the $97^{th}$ Thr (T), the $99^{th}$ Asn (N), and the $100^{th}$ Ala (A) from the N-terminus of BRIL or an antigen-binding fragment thereof, (g) an antibody which binds to at least one amino acid residue selected from amino acid residues of the $74^{th}$ Asp (D), the $92^{nd}$ Glu (E), the $96^{th}$ Thr (T), the $97^{th}$ Thr (T), and the $99^{th}$ Asn (N) from the N-terminus of BRIL or an antigen-binding fragment thereof, (h) an antibody which binds to the $74^{th}$ Asp (D) from the N-terminus of BRIL or an antigen-binding fragment thereof, (i) an antibody which binds to at least one amino acid residue selected from amino acid residues of the $92^{nd}$ Glu (E), the $96^{th}$ Thr (T), the $97^{th}$ Thr (T), and the $99^{th}$ Asn (N) from the N-terminus of BRIL or an antigen-binding fragment thereof, (j) an antibody which binds to the $92^{nd}$ Glu (E) from the N-terminus of BRIL or an antigen-binding fragment thereof, (k) an antibody which binds to the $96^{th}$ Thr (T) from the N-terminus of BRIL or an antigen-binding fragment thereof, (l) an antibody which binds to the $97^{th}$ Thr (T) from the N-terminus of BRIL or an antigen-binding fragment thereof, (m) an antibody which binds to the $99^{th}$ Asn (N) from the N-terminus of BRIL or an antigen-binding fragment thereof, (n) an antibody which binds to amino acid residues of the $96^{th}$ Thr (T), the $97^{th}$ Thr (T), and the $99^{th}$ Asn (N) from the N-terminus of BRIL or an antigen-binding fragment thereof, and (o) an antibody which binds to the amino acid residues of the $92^{nd}$ Glu (E), the $96^{th}$ Thr (T), the $97^{th}$ Thr (T), and the $99^{th}$ Asn (N) of BRIL or antigen-binding fragment thereof.

In the present invention, as the amino acid sequence constituting the helix structure of BRIL, among the amino acid sequences represented by SEQ ID NO: 9, amino acid sequences from the $4^{th}$ M to the $19^{th}$ K from the N-terminus as the amino acid sequences constituting the first helix structure, the amino acid sequences from the $23^{rd}$ A to the $42^{nd}$ K from the N-terminus as the amino acid sequences constituting the second helix structure, amino acid sequences from the $59^{th}$ K to $81^{st}$ E from the N-terminus as the amino acid sequences constituting the third helix structure, and amino acid sequences from the $84^{th}$ V to the $105^{th}$ Y from the N-terminus as the amino acid sequences constituting the fourth helix structure are exemplified.

More specifically, the antibody or the antibody fragment of the present invention includes any one selected from the following (i) to (vii).

(i) an antibody which binds by competing with an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, or an antigen-binding fragment thereof, (ii) an antibody which binds to an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof, (iii) an antibody which binds to the same epitope as an epitope to which an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, binds or an antigen-binding fragment thereof (iv) an antibody in which CDRs 1 to 3 of VH of the antibody contain the amino acid sequences having homology of preferably, in the following order, 90% or more, 91% or more, 92% or more, 93% or more, and 94% or more, and is more preferably 95% or more, 96% or more, 97% or more, 98% or more, and 99% or more with the amino acid sequences represented by SEQ ID NOs: 1 to 3, respectively, and in which CDRs 1 to 3 of VL of the antibody contain the amino acid sequences having homology of preferably, in the following order, 90% or more, 91% or more, 92% or more, 93% or more, and 94% or more, and is more preferably 95% or more, 96% or more, 97% or more, 98% or more, and 99% or more with the amino acid sequences represented by SEQ ID NOs: 4 to 6, respectively, and an antigen-binding fragment thereof, (v) an antibody in which CDRs 1 to 3 of VH of the antibody contain the amino acid sequences represented by SEQ ID NOs: 1 to 3, respectively, and in which CDRs 1 to 3 of VL of the antibody contain the amino acid sequences represented by SEQ ID NOs: 4 to 6, respectively, or an antigen-binding fragment thereof, (vi) an antibody in which VH of the antibody contains the amino acid sequence having homology of preferably, in the following order, 90% or more, 91% or more, 92% or more, 93% or more, and 94% or more, and is more preferably 95% or more, 96% or more, 97% or more, 98% or more, and 99% or more with the amino acid sequence represented by SEQ ID NO: 7, and in which VL of the antibody contains the amino acid sequence having homology of preferably, in the following order, 90% or more, 91% or more, 92% or more, 93% or more, and 94% or more, and is more preferably 95% or more, 96% or more, 97% or more, 98% or more, and 99% or more with the amino acid sequence represented by SEQ ID NO: 8, or an antigen-binding fragment thereof, and (vii) an antibody in which VH of the antibody contains the amino acid sequence represented by SEQ ID NO: 7 and VL of the antibody contains the amino acid sequence represented by SEQ ID NO: 8 or an antigen-binding fragment thereof.

The antibody of the present invention also includes derivatives obtained by fusing molecules necessary for structural analysis such as fluorescent substances and radioisotopes to the antibody or the antigen-binding fragments thereof of the present invention. The antibody or the antigen-binding fragment thereof of the present invention can be used for detection or measurement of BRIL fusion protein. For example, as an immunological detection or measurement, a labeled antigen or antibody or antigen-binding fragment thereof is used to detect or measure the amount of antibody or antigen-binding fragment, or the amount of antigen.

Examples of immunological detection or measurement methods include a radiolabeled immunoassay (RIA) method, an enzyme immunoassay (EIA or ELISA) method, a fluorescence immunoassay (FIA) method, a luminescent immunoassay method, a western blot method, and a physicochemical method.

According to the above methods, not only the BRIL fusion protein can be detected or measured, but also in the structural analysis of BRIL fusion protein by electron microscope and the crystallography by X-ray, the BRIL part fused to the target protein can be labeled with an anti-BRIL antibody, or the orientation of the molecule under three dimensions can be determined.

Hereinafter, a method of producing an anti-BRIL antibody of the present invention, a method of stabilizing a BRIL fusion protein using the anti-BRIL antibody, a method of analyzing a crystal structure of the BRIL fusion protein, and the like will be specifically described.

1. Production Method of Antibody (1) Preparation of Antigen

A BRIL fusion protein in which BRIL is fused to a BRIL protein as an antigen or a target protein can be obtained by introducing an expression vector containing cDNA that encodes the full length of the protein or a partial length thereof into E. coli, yeast, insect cells, animal cells, or the like.

Furthermore, a synthetic peptide having a partial sequence of BRIL can be prepared using a chemical synthesis method such as the Fmoc method or the tBoc method and used as an antigen. A known tag such as FLAG or His may be added to the C-terminus or the N-terminus of BRIL or BRIL fusion protein.

BRIL or the BRIL fusion protein used in the invention can be produced using the method described in Molecular Cloning, A Laboratory Manual, Second Edition, Cold Spring Harbor Laboratory Press (1989), Current Protocols In Molecular Biology, John Wiley & Sons (1987-1997) or the like or another method by expressing DNA that encodes BRIL or the BRIL fusion protein in a host cell for example by the following method.

First, a recombinant vector is produced by inserting the full-length cDNA containing the part that encodes BRIL or the BRIL fusion protein into downstream of a promoter in an appropriate expression vector. A transformant that produces the polypeptide can be obtained by introducing the obtained recombinant vector into a host cell suitable for the expression vector.

As the expression vector, any vector can be used as long as it can replicate autonomously or can be inserted into a chromosome in a host cell to be used and which contains a suitable promoter in the position that enables the transcription of DNA that encodes the polypeptide.

As the host cell, any cell, such as a microorganism belonging to the genus *Escherichia* such as *E. coli*, Pichia pastoris yeast, an insect cell such as Sf9 or an animal cell such as CHO cell can be used as long as it enables the expression of a target gene.

In a case where a prokaryote such as *E. coli* is used as a host cell, the recombinant vector is preferably a vector that can replicate autonomously in the prokaryote and that contains a promoter, a ribosomal binding sequence, DNA containing the part encoding BRIL or the BRIL fusion protein and a transcription termination sequence. In addition, the transcription termination sequence is not essentially needed for the recombinant vector, but the transcription termination sequence is preferably placed immediately after the structural gene. Furthermore, the recombinant vector may contain a gene that controls the promoter. As the expression vector, it is preferable to use a plasmid in which the distance between the Shine-Dalgarno sequence (also called SD sequence) that is a ribosomal binding sequence and the initiation codon is appropriately adjusted (to, for example, 6 to 18 nucleotides).

In addition, regarding the nucleotide sequence of DNA that encodes BRIL or the BRIL fusion protein, a nucleotide can be substituted in a manner that the codon becomes optimum for the expression in a host, which enables the enhancement in the production rate of target BRIL or BRIL fusion protein.

As the expression vector, any vector can be used as long as it can exhibit its function in a host cell to be used. Examples thereof include pBTrp2, pBTac1, and pBTac2 (produced by Roche Diagnostics K.K.), pKK233-2 (produced by Pharmacia), pSE280 (produced by Invitrogen), pGEMEX-1 (produced by Promega Corporation), pQE-8 (produced by QIAGEN), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK(−) (produced by Stratagene Corporation), pTrs30 [prepared from *E. coli* JM109/pTrS30 (FERM BP-5407)], pTrs32 [prepared from *E. coli* JM109/pTrS32 (FERM BP-5408)], pGHA2 [prepared from *E. coli* IGHA2 (FERM BP-400), JP-A-S60-221091], pGKA2 [prepared from *E. coli* IGKA2 (FERM BP-6798), JP-A-S60-221091], pTerm2 (U.S. Pat. Nos. 4,686,191, 4,939,094 and 5,160, 735), pSupex, pUB110, pTP5, pC194, pEG400 [J. Bacteriol., 172, 2392 (1990)], pGEX (produced by Pharmacia), pET System (produced by Novagen), pME18SFL3, and pFastBac1 (produced by Invitrogen).

Examples of the host cell include *E. coli* XL1-Blue, *E. coli* XL2-Blue, *E. coli* DH1, *E. coli* MC1000, *E. coli* KY3276, *E. coli* W1485, *E. coli* JM109, *E. coli* HB101, *E. coli* No. 49, *E. coli* W3110, *E. coli* NY49, *E. coli* DH5α and the like.

As a method for introducing a recombinant vector into a host cell, any method can be used as long as it is a method by which DNA is introduced into a host cell to be used. Examples thereof include a method using calcium ions [Proc. Natl. Acad. Sci. USA, 69, 2110 (1972), Gene, 17, 107 (1982) and Molecular & General Genetics, 168, 111 (1979)].

In a case of using an animal cell as a host, as the expression vector, any vector can be used as long as it can exhibit its function in the animal cell. Examples thereof include pcDNAI, pCDM8 (produced by Funakoshi Co., Ltd.), pAGE107 [JP-A-H3-22979; and Cytotechnology, 3, 133 (1990)], pAS3-3 (JP-A-H2-227075), pCDM8 [Nature, 329, 840 (1987)], pcDNAI/Amp (produced by Invitrogen), pcDNA3.1 (produced by Invitrogen), pREP4 (produced by Invitrogen), pAGE103 [J. Biochemistry, 101, 1307 (1987)], pAGE210, pME18SFL3, pKANTEX93 (International Publication No. 97/10354), N5KG1val (U.S. Pat. No. 6,001,358), INPEP4 (produced by Biogen-IDEC), a transposon vector (International Publication No. 2010/143698) and the like.

Examples of the host cell include a human leukemia cell Namalwa, a monkey cell COS, a Chinese hamster ovary cell CHO [Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci., 60, 1275 (1968); Cell, 6, 121 (1975); and Molecular Cell Genetics, Appendix I, II (pp. 883-900)]; a CHO cell which lacks dihydrofolate reductase gene (referred to as dhfr below) (CHO/DG44 cell) [Proc. Natl. Acad. Sci. USA, 77, 4216 (1980)], CHO-K1 (ATCC CCL-61), DUkXB11 (ATCC CCL-9096), Pro-5 (ATCC CCL-1781), CHO-S (Life Technologies, Cat #11619), Pro-3, a rat myeloma cell YB2/3HL.P2.G11.16Ag.20 (also referred to as YB2/0), a mouse myeloma cell NSO, a mouse myeloma cell SP2/0-Ag14, a Syrian hamster cell BHK, HBT5637 (JP-A-S63-000299) and the like.

As a method of introducing an expression vector into a host cell, any method can be used as long as it is a method by which DNA is introduced into an animal cell. Examples thereof include the electroporation [Cytotechnology, 3, 133 (1990)], the calcium phosphate transfection method (JP-A-H2-227075), the lipofection [Proc. Natl. Acad. Sci. USA, 84, 7413 (1987)] and the like.

BRIL or the BRIL fusion protein can be produced by culturing a transformant derived from a microorganism, yeast, insect cell or animal cell having the recombinant vector into which DNA that encodes BRIL or the BRIL fusion protein has been introduced and which is obtained as above in a medium, generating and accumulating BRIL or the BRIL fusion protein in the culture solution and then collecting BRIL or the BRIL fusion protein from the culture solution. A method of culturing the transformant in a medium can be performed according to a usual method used for a host culture.

Examples of the method of expressing a gene that encodes BRIL or the BRIL fusion protein include a method such as secretory production or fusion protein expression [Molecular Cloning, A Laboratory Manual, Second Edition, Cold Spring Harbor Laboratory Press (1989)] in addition to direct expression. Examples of the method of producing BRIL or the BRIL fusion protein include a method of producing in a host cell, a method of secretion out of a host cell and a method of producing on the outer membrane of a host cell. An appropriate method can be selected by changing the host cell to be used or the structure of BRIL or the BRIL fusion protein to be produced.

(2) Immunization of Animal and Preparation of Antibody-Producing Cell for Fusion By immunizing a 3- to 20-week old animal such as a mouse, an immunodeficient mouse (MRL/MpJJms slc-lpr/lpr), a rat, a rabbit or a hamster with the antigen obtained in (1), antibody-producing cells are collected from the spleen, lymph nodes or peripheral blood of the animal.

Immunization is performed by administering the antigen for example together with an appropriate adjuvant such as Freund's complete adjuvant, aluminum hydroxide gel, *Bordetella pertussis* vaccine or proteoliposome subcutaneously, intravenously or intraperitoneally to the animal. In a case where the antigen is a partial peptide, a conjugate of the antigen with a carrier protein such as BSA (bovine serum albumin) or KLH (Keyhole Limpet hemocyanin) is produced and used as an immunogen.

The administration of the antigen is performed 5 to 10 times every 1 to 2 weeks after the first administration. On the $3^{rd}$ to $7^{th}$ day after each administration, the blood is collected from a venous plexus of the fundus of the eye, and the antibody valency of the serum is measured using an enzyme immunoassay method [Antibodies—A Laboratory Manual, Cold Spring Harbor Laboratory (1988)] or the like. An animal in which the serum exhibited sufficient antibody valency with respect to the antigen used for the immunization is used as a supply source for the antibody-producing cells for fusion.

On the $3^{rd}$ to $7^{th}$ day after a final administration of the antigen, tissues including the antibody-producing cells such as the spleen are extracted from the immunized animal, and the antibody-producing cells are collected. In a case of using the spleen cells, the spleen is shredded and loosened, followed by centrifugation, and then erythrocytes are removed. The antibody-producing cells for fusion are thus obtained.

(3) Preparation of Myeloma Cells

As the myeloma cells, established cells obtained from a mouse are used, and for example, a 8-azaguanine resistant mouse (BALB/c derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14(SP-2) [Nature, 276, 269 (1978)], P3-X63-Ag8653 (653) [J. Immunology, 123, 1548 (1979)], P3-X63-Ag8(X63) [Nature, 256, 495 (1975)] or the like is used.

The myeloma cells are subjected to subculturing with a normal medium [RPMI1640 medium supplemented with glutamine, 2-mercaptoethanol, gentamicin, FBS and 8-azaguanine] and subjected to subculturing with a normal medium 3 to 4 days before the cell fusion, and $2 \times 10^7$ or more cells are acquired on the day of the fusion.

(4) Cell Fusion and Preparation of Monoclonal Antibody-Producing Hybridoma

The antibody-producing cells for fusion obtained in (2) and the myeloma cells obtained in (3) are thoroughly washed with the Minimum Essential Medium (MEM) or PBS (disodium phosphate 1.83 g, monopotassium phosphate 0.21 g, salt 7.65 g, distilled water 1 liter, pH 7.2), mixed at cell numbers of antibody-producing cells for fusion:myeloma cells of 5:1 to 10:1 and centrifuged, and then the supernatant is removed.

After the precipitated cell clusters are loosened thoroughly, a mixture of polyethylene glycol-1000 (PEG-1000), MEM and dimethyl sulfoxide is added thereto while stirring at 37° C. Furthermore, 1 to 2 mL of MEM is added thereto every 1 to 2 minutes for several times, and then MEM is added so that the total amount becomes 50 mL. After centrifugation, the supernatant is removed. The precipitated cell clusters are loosened gently, and then the cells, as the antibody-producing cells for fusion, are suspended gently in the HAT medium [normal medium supplemented with hypoxanthine, thymidine and aminopterin].

This suspension is cultured in a 5% $CO_2$ incubator at 37° C. for 7 to 14 days. After culturing, a part of the culture supernatant is taken, and cell clusters which react with an antigen containing BRIL or BRIL fusion protein and which do not react with antigen not containing BRIL or BRIL fusion protein are selected by a method of selecting a hybridoma such as the binding assay described below. Next, after cloning by the limiting dilution method, a hybridoma which stably shows potent antibody valency is selected as a monoclonal antibody-producing hybridoma.

(5) Preparation of Purified Monoclonal Antibody

The monoclonal antibody-producing hybridoma obtained in (4) is intraperitoneally injected into an 8- to 10-week old mouse or nude mouse which has been treated by pristane treatment [by intraperitoneally administering 2,6,10,14-tetramethylpentadecane (Pristane) 0.5 mL and breeding for 2 weeks]. In 10 to 21 days, the hybridoma becomes an ascites tumor. The ascites are collected from this mouse, and the solid is removed by centrifugation. Then, by salting out with 40 to 50% ammonium sulfate and purifying by caprylic acid precipitation method, a DEAE-Sepharose column, a protein A-column or a gel filtration column, an IgG or IgM fraction is collected to obtain a purified monoclonal antibody.

Moreover, the monoclonal antibody-producing hybridoma obtained in (4) is cultured in RPMI1640 medium supplemented with 10% FBS or the like, and then the supernatant is removed by centrifugation. The hybridoma is suspended in Hybridoma SFM medium and cultured for 3 to 7 days. A purified monoclonal antibody can also be obtained by centrifuging the obtained cell suspension, purifying from the obtained supernatant by a protein A-column or a protein G-column and collecting an IgG fraction. In this regard, 5% Daigo's GF21 can be added to Hybridoma SFM medium.

The subclass of the antibody is determined by the enzyme immunoassay method using a subclass typing kit. The protein mass is determined by the Lowry method or by calculating from the absorbance at 280 nm.

(6) Selection of Monoclonal Antibody

As described below, the monoclonal antibody is selected by measuring the binding property of the antibody to BRIL or BRIL fusion protein expressing cells using binding ELISA, liposome ELISA, and flow cytometry. BRIL or the BRIL fusion protein expressing cells may be any cell as long as BRIL or the BRIL fusion protein is expressed on the cell surface, and examples thereof include Sf9 cells, Pichia Pastoris cells, human cell lines, and BRIL fusion protein forced expression cell lines obtained from (1).

After dispensing the BRIL fusion protein, the liposome, or the BRIL fusion protein expressing cells to a plate such as a 96-well plate, and the substances to be tested such as serum, culture supernatants of hybridomas or purified monoclonal antibodies are dispensed as the first antibodies and reacted.

The cells after the reaction are thoroughly washed with PBS containing 1% to 10% bovine serum albumin (BSA) (hereinafter, referred to as BSA-PBS), and then, as a second antibody, an anti-immunoglobulin antibody labeled with a fluorescent reagent or the like is dispensed and reacted. After thoroughly washing with BSA-PBS or the like, by measuring the amount of fluorescence of the labeled antibody using a flow cytometer, the monoclonal antibody that reacts specifically with the BRIL fusion protein, the BRIL fusion protein liposome, or the BRIL fusion protein expressing cell is selected.

In addition, the antibody that competes with the antibody of the present invention and binds to the BRIL fusion protein, the BRIL fusion protein liposome, or the BRIL fusion protein expressing cell can be obtained by adding an antibody to be tested to a measurement system using the binding ELISA, liposome ELISA, or flow cytometry described above.

That is, by screening an antibody which inhibits binding of the antibody of the invention and the BRIL fusion protein, the BRIL fusion protein liposome, or the BRIL fusion protein expressing cell when the antibody to be tested is added, a monoclonal antibody that competes with the antibody of the invention in binding to the amino acid sequence of BRIL or the BRIL fusion protein or the three-dimensional structure of BRIL or the BRIL fusion protein can be obtained.

In addition, an antibody which binds to an epitope containing the epitope to which the monoclonal antibody binding to BRIL or the BRIL fusion protein of the invention binds can be obtained by identifying the epitope of the antibody obtained by the screening method described above by a known method, producing a synthetic peptide containing the identified epitope, a synthetic peptide which mimics the three-dimensional structure of the epitope or the like, and immunizing.

Furthermore, an antibody which binds to the same epitope as the epitope to which the monoclonal antibody binding to BRIL or the BRIL fusion protein of the invention binds can be obtained by identifying the epitope of the antibody obtained by the screening method described above, producing a partially synthetic peptide of the identified epitope, a synthetic peptide which mimics the three-dimensional structure of the epitope or the like, and immunizing.

2. Production of Genetically Recombinant Antibody

As examples for producing a genetically recombinant antibody, methods for producing a human chimeric antibody are described below. Genetically recombinant mouse antibody, rat antibody, rabbit antibody, and the like can also be produced by the same method.

(1) Construction of Expression Vector for Genetically Recombinant Antibody

An expression vector for a genetically recombinant antibody is an expression vector for animal cells in which DNA that encodes CH and CL of various antibodies such as a mouse, a rat, or a human has been incorporated and can be constructed by cloning DNAs that encode CH and CL of an any desired kind of antibody into an expression vector for animal cells.

As the C region of the antibody, CH and CL of any antibody such as mouse, rat, rabbit, and human can be used. For example, CH of γ1 subclass and CL of κ class of a human antibody and the like are used. As the DNAs that encode CH and CL of the human antibody, cDNA is used, but chromosomal DNA consisting of exons and introns can also be used.

As the expression vector for animal cells, any vector can be used as long as it is capable of incorporating and expressing a gene that encodes the C region of a human antibody. For example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)] or the like are used.

The promoter and the enhancer of the expression vector for animal cells are the early promoter of SV40 [J. Biochem., 101, 1307 (1987)], the Moloney murine leukemia virus LTR [Biochem. Biophys. Res. Commun., 149, 960 (1987)] or the promoter of immunoglobulin H chain [Cell, 41, 479 (1985)] and the enhancer [Cell, 33, 717 (1983)] or the like.

As the expression vector for the genetically recombinant antibody, an expression vector for a genetically recombinant antibody of a type in which the antibody H chains and L chains are on the same vector (tandem type) [J. Immunol. Methods, 167, 271 (1994)] is used from the viewpoints of ease of construction of the expression vector for the genetically recombinant antibody, ease of introduction into animal cells, balanced expression levels of the antibody H chains and L chains in animal cells and the like, but a type in which the antibody H chains and L chains are on different vectors can also be used. As the tandem type expression vector for a genetically recombinant antibody, pKANTEX93 (International Publication No. 97/10354), pEE18 [Hybridoma, 17, 559 (1998)] and the like are used.

(2) Acquisition of cDNA Encoding V Region of Antibody Derived from Human or Animal Other than Human and Analysis of Amino Acid Sequence cDNA that encodes VH and VL of a non-human antibody can be obtained, and the amino acid sequence can be analyzed as follows.

mRNA is extracted from hybridoma cells producing a non-human antibody, and cDNA is synthesized. The synthesized cDNA is cloned into a vector such as a phage or a plasmid to produce a cDNA library. Recombinant phages or recombinant plasmids having cDNAs that encode VH or VL are isolated from the libraries using DNAs that encode the C region and the V region of the mouse antibody as probes. The entire nucleotide sequences of VH or VL of the target mouse antibody on the recombinant phages or the recombinant plasmids are determined, and then the entire amino acid sequences of VH or VL are deduced from the nucleotide sequences.

As the animal other than human which produces the hybridoma cells producing the non-human antibody, a mouse, a rat, a hamster, a rabbit, or the like is used, but any animal can be used as long as hybridoma cells can be produced.

The selected cDNA is cleaved with an appropriate restriction enzyme or the like and then cloned into a plasmid such as pBluescript SK (−) (manufactured by Stratagene), and the nucleotide sequence of the cDNA is determined by a commonly used nucleotide sequence analysis method or the like. For the nucleotide sequence analysis method, for example, after performing a reaction such as the dideoxy method [Proc. Natl. Acad. Sci. USA, 74, 5463 (1977)], an automatic nucleotide sequence analyzer such as ABI PRISM3700 (manufactured by PE Biosystems) or A.L.F. DNA sequencer (manufactured by Pharmacia) or the like is used.

By deducing the entire amino acid sequences of VH and VL from the determined nucleotide sequences and comparing with the entire amino acid sequences of VH and VL of a known antibody [Sequences of Proteins of Immunological Interest, US Dept. Health and Human Services (1991)], it is confirmed whether the obtained cDNA encodes the complete amino acid sequences of VH and VL of an antibody containing a secretion signal sequence.

Regarding the complete amino acid sequences of VH and VL of the antibody containing a secretion signal sequence, by comparing with the entire amino acid sequences of VH and VL of a known antibody [Sequences of Proteins of Immunological Interest, US Dept. Health and Human Services (1991)], the length of the secretion signal sequence and the N-terminus amino acid sequence can be deduced, and the subgroup to which they belong can be found. In addition, the amino acid sequences of the CDRs of VH and VL can also be determined by comparing with the amino acid sequences of VH and VL of a known antibody [Sequences of Proteins of Immunological Interest, US Dept. Health and Human Services (1991)].

(3) Construction of Expression Vector for Genetically Recombinant Antibody

By cloning cDNAs that encode VH and VL of a non-human antibody or a human antibody in the upstream of the respective genes that encode CH and CL of a non-human antibody or a human antibody in the expression vector for a genetically recombinant antibody obtained in (1), the expression vector for a genetically recombinant antibody such as a mouse, a rat, a rabbit, and a human chimeric antibody can be constructed.

In order to link the 3' terminus sides of the cDNAs that encode VH or VL of the non-human antibody or a human antibody with the respective 5' terminus sides of CH or CL of the non-human antibody or the human antibody, cDNAs of VH and VL in which the nucleotide sequences of the linking parts are designed to encode an appropriate amino acid and to become an appropriate restriction enzyme recognition sequence are produced.

The produced cDNAs of VH and VL are cloned in the upstream of the respective genes that encode CH or CL of the non-human antibody or the human antibody in the expression vector for a genetically recombinant antibody obtained in (1) in a manner that they are expressed in an appropriate form, and therefore an expression vector for a genetically recombinant antibody such as a mouse, a rat, a rabbit, and a human chimeric antibody can be constructed.

The genetically recombinant antibody can be produced by introducing and expressing the constructed expression vector for genetically recombinant antibody into the appropriate host cell described above.

3. Applications of Antibody Binding to BRIL or BRIL Fusion Protein

The antibody of the present invention is used applications for an immunological method, a method of stabilizing a target protein, a crystal production method, a crystallography method, and an electron microscope structural analysis, by utilizing the property of specifically binding to BRIL or the BRIL fusion protein. The immunological method is a method of detecting or measuring the amount of an antibody or the amount of an antigen using a labeled antigen, antibody or the like. For example, the radioactive material labeled immune antibody method, the enzyme immunoassay method, the fluorescence immunoassay method, the luminescence immunoassay method, the western blotting method, the physicochemical method or the like is used.

In addition, in the structural analysis such as a crystal production method, an electron microscope structural analysis, and a crystallography, it can be used by stabilizing the BRIL fusion protein using an unlabeled antibody. Further, in this structural analysis, the anti-BRIL antibody itself is useful because it can be recognized as a label in a complex by specifically binding to BRIL or the BRIL fusion protein.

In the radioactive material labeled immune antibody method, for example, the antibody or the antibody fragment of the invention is reacted with an antigen, cells expressing an antigen or the like and then reacted with an anti-immunoglobulin antibody or an antibody fragment thereof subjected to radiolabeling, followed by measurement with a scintillation counter or the like.

In the enzyme immunoassay method, for example, the antibody or the antibody fragment of the invention is reacted with an antigen, cells expressing an antigen or the like and then reacted with an anti-immunoglobulin antibody or a binding fragment thereof subjected to labeling with an enzyme or the like, followed by addition of a substrate and measurement of the absorbance of the reaction solution with an absorptiometer. As a labeling substance used in the enzyme immunoassay method, a known [Enzyme Immunoassay Method, Igaku-Shoin Ltd. (1987)] enzyme label can be used. As an enzyme label, an alkaline phosphatase label, a peroxidase label, a luciferase label, a biotin label or the like is used.

In the fluorescence immunoassay method, measurement is carried out by the method described in documents [Monoclonal Antibodies-Principles and practice, Third edition, Academic Press (1996) and A manual for monoclonal antibody experiments, Kodansha scientific books (1987)] or the like. As the labeling substance used in the fluorescence immunoassay method, a known [Fluorescent Antibody Method, Soft Science (1983)] fluorescent label can be used. For example, FITC, RITC or the like is used. In the luminescence immunoassay method, measurement is carried out by the method described in a document [Bioluminescence and Chemiluminescence, Clinical Test 42, Hirokawa-Shoten Ltd. (1998)] or the like. As the labeling substance used in the luminescence immunoassay method, a known luminescent label is used, and an acridinium ester, a lophine or the like is used.

In addition, detection can be carried out by the fluorescent antibody staining method in which a fluorescently-labeled antibody is reacted with cells and analyzed with a flow cytometer [Monoclonal Antibodies—Principles and practice, Third edition, Academic Press (1996) and A manual for monoclonal antibody experiments, Kodansha scientific books (1987)]. In addition, when the FMAT 8100 HTS system (manufactured by Applied Biosystems) or the like of the fluorescent antibody staining methods is used, the amount of an antigen or the amount of an antibody can be measured without separating the formed antibody-antigen complex from the free antibody or antigen that is not involved in formation of the antibody-antigen complex.

As the method of stabilizing the BRIL fusion protein using the anti-BRIL antibody of the present invention, the crystal production method, and the crystal structural analysis method, for example, after preparing an antibody which specifically binds to BRIL or an antibody fragment and reacting with the BRIL fusion protein at an appropriate molar ratio, the peak of the complex consisting of the BRIL fusion protein and the anti-BRIL antibody is purified and crystallized using liquid chromatography so that the anti-BRIL antibody binds to the BRIL fusion protein, and thereby it is possible to obtain stabilized co-crystal of the BRIL fusion protein/anti-BRIL antibody.

The obtained BRIL fusion protein is stably crystallized and can be used for X-ray crystallography.

In addition, as a method of stabilizing the BRIL fusion protein in a solution using the anti-BRIL antibody of the present invention, for example, in the structural analysis such as negative stain electron microscopy or cryo electron microscope analysis, by adding the anti-BRIL antibody to the sample BRIL fusion protein to perform the electron microscope analysis, the BRIL fusion protein in the solution can be stabilized and used as a marker for the structural complex so as to impart molecular orientation in three dimensions. As the anti-BRIL antibody, any of the above-mentioned labeled and non-labeled antibodies can be used. Both of the negative stain electron microscopy and the cryo electron microscope analysis are methods of analyzing the structure of the target protein in the liquid phase, and the samples that can be analyzed using the negative stain electron microscope can also be used structurally analyzed in the cryo electron microscope.

Hereinafter, the present invention will be specifically described with reference to examples, but the present invention is not limited to the following examples.

EXAMPLES

Example 1

Production of BRIL Fusion Human ChemR23 Protein

From the previously reported crystallographic results of GPCRs, it is known that the structural stability of GPCR is improved and the crystallization probability is increased by fusing BRIL to a portion where the $16^{th}$ to $24^{th}$ amino acid regions counted from proline stored in the $5^{th}$ transmembrane helix of GPCR and the $-24^{th}$ to $-28^{th}$ amino acid regions counted from the proline stored in the $6^{th}$ transmembrane helix overlap (Eugene Chun et al. Structure, 2012; 20: 967-976). Therefore, also in this Example, a human ChemR23-BRIL fusion protein was constructed by inserting BRIL into a loop portion between the $5^{th}$ and $6^{th}$ transmembrane helices of human ChemR23 (hereinafter, also abbreviated as hChemR23).

Specifically, in the amino acid sequence (SEQ ID NO: 10) of hChemR23, 32 kinds of BRIL fusion proteins such as a mutant in which BRIL is inserted between the $247^{th}$ leucine and the $248^{th}$ glutamine, a mutant having BRIL inserted between the $248^{th}$ glutamine and the $249^{th}$ arginine, a mutant in which BRIL is inserted between the $249^{th}$ arginine and the $250^{th}$ asparagine, a mutant having BRIL inserted between the $250^{th}$ asparagine and the $251^{st}$ arginine, a mutant in which BRIL is inserted between the $251^{st}$ arginine and the $252^{nd}$ leucine, a mutant in which BRIL is inserted between $252^{nd}$ leucine and $253^{rd}$ alanine, a mutant having BRIL inserted between the $253^{rd}$ alanine and the $254^{th}$ lysine, a mutant in which BRIL is inserted between 254$^{th}$ lysine and 255$^{th}$ threonine, a mutant in which the 248$^{th}$ glutamine to the 254$^{th}$ lysine are deleted and BRIL is inserted between the 247$^{th}$ leucine and the 255$^{th}$ threonine, a mutant in which 248$^{th}$ glutamine to 253$^{rd}$ alanine are deleted and BRIL is inserted between 247$^{th}$ leucine and 254$^{th}$ lysine, a mutant in which 248$^{th}$ glutamine to 252$^{nd}$ leucine are deleted and BRIL is inserted between 247$^{th}$ leucine and 253$^{rd}$ alanine, a mutant in which the 248$^{th}$ glutamine to the 251$^{st}$ arginine are deleted and BRIL is inserted between the 247$^{th}$ leucine and the 252$^{nd}$ leucine, a mutant in which the 248$^{th}$ glutamine to the 250$^{th}$ asparagine are deleted and BRIL is inserted between the 247$^{th}$ leucine and the 251$^{st}$ arginine, a mutant in which 248$^{th}$ glutamine to 249$^{th}$ arginine are deleted and BRIL is inserted between 247$^{th}$ leucine and 250$^{th}$ asparagine, a mutant in which 248$^{th}$ glutamine is deleted and BRIL is inserted between 247$^{th}$ leucine and 249$^{th}$ arginine, a mutant in which the 249$^{th}$ arginine to the 254$^{th}$ lysine are deleted and BRIL is inserted between the 248$^{th}$ glutamine and the 255$^{th}$ threonine, a mutant in which 249$^{th}$ arginine to 253$^{rd}$ alanine are deleted and BRIL is inserted between 248$^{th}$ glutamine and 254$^{th}$ lysine, a mutant in which 249$^{th}$ arginine to 252$^{nd}$ leucine are deleted and BRIL is inserted between 248$^{th}$ glutamine and 253$^{rd}$ alanine, a mutant in which 249$^{th}$ arginine to 251$^{st}$ arginine are deleted and BRIL is inserted between 248$^{th}$ glutamine and 252$^{nd}$ leucine, a mutant in which the 249$^{th}$ arginine to 250$^{th}$ asparagine are deleted and BRIL is inserted between 248$^{th}$ glutamine and 251$^{st}$ arginine, a mutant in which the 249$^{th}$ arginine is deleted and BRIL is inserted between 248$^{th}$ glutamine and 250$^{th}$ asparagine, a mutant in which the 250$^{th}$ asparagine to the 254$^{th}$ lysine are deleted and BRIL is inserted between the 249$^{th}$ arginine and the 255$^{th}$ threonine, a mutant in which the 250$^{th}$ asparagine to the 253$^{rd}$ alanine are deleted and BRIL is inserted between the 249$^{th}$ arginine and the 254$^{th}$ lysine, a mutant in which the 250$^{th}$ asparagine to the 252$^{nd}$ leucine are deleted and BRIL is inserted between the 249$^{th}$ arginine and the 253$^{rd}$ alanine, a mutant in which the 250$^{th}$ asparagine to the 251$^{st}$ arginine are deleted and BRIL is inserted between the 249$^{th}$ arginine and the 252$^{nd}$ leucine, a mutant in which the 250$^{th}$ asparagine is deleted and BRIL is inserted between the 249$^{th}$ arginine and 251$^{st}$ arginine, a mutant in which the 251$^{st}$ arginine to the 254$^{th}$ lysine are deleted and BRIL is inserted between the 250$^{th}$ asparagine and the 255$^{th}$ threonine, a mutant in which the 251$^{st}$ arginine to the 253$^{rd}$ alanine are deleted and BRIL is inserted between the 250$^{th}$ asparagine and the 254$^{th}$ lysine, a mutant in which the 251$^{st}$ arginine to the 252$^{nd}$ leucine are deleted and BRIL is inserted between the 250$^{th}$ asparagine and the 253$^{rd}$ alanine, a mutant in which 251$^{st}$ arginine is deleted and BRIL is inserted between 250$^{th}$ asparagine and 252$^{nd}$ leucine, a mutant in which the 252$^{nd}$ leucine to the 254$^{th}$ lysine are deleted and BRIL is inserted between the 251$^{st}$ arginine and the 255$^{th}$ threonine, a mutant in which the 252$^{nd}$ leucine to the 253$^{rd}$ alanine are deleted and BRIL is inserted between the 251$^{st}$ arginine and the 254$^{th}$ lysine, a mutant in which 252$^{nd}$ leucine is deleted and BRIL is inserted between 251$^{st}$ arginine and 253$^{rd}$ alanine, a mutant in which the 253$^{rd}$ alanine to the 254$^{th}$ lysine are deleted and BRIL is inserted between the 252$^{nd}$ leucine and the 255$^{th}$ threonine, a mutant in which 253$^{rd}$ alanine is deleted and BRIL is inserted between 252$^{nd}$ leucine and 254$^{th}$ lysine, and a mutant in which 254$^{th}$ lysine is deleted and BRIL is inserted between 253$^{rd}$ alanine and 255$^{th}$ threonine were produced from the N-terminus.

A system in which a fragmented vector (vector in which TEV protease recognition sequence, GFP and His$_8$ tag sequence are inserted into p426GAL1) in Saccharomyces cerevisiae and a gene fragment are linked by homologous recombination reaction (Nat. Protoc. 2008; 784-98) was used to express BRIL fusion proteins in which green fluorescent protein (GFP) and His$_8$ tag sequences were fused to the C-terminus of human ChemR23.

The expressed hChemR23-BRIL fusion proteins were subjected to fluorescent size exclusion chromatography (FSEC), and FSEC screening was performed. A sample with a higher desired main peak and higher monodispersity compared to the aggregate peak was determined to be expressed as a single BRIL fusion protein, and selected as a BRIL fusion protein in which BRIL was inserted at an optimal insertion position.

Furthermore, hChemR23-BRIL fusion proteins in which the lengths of the N-terminus and C-terminus amino acid sequences of the BRIL fusion protein were changed were produced, and the optimal lengths of the N-terminus and C-terminus amino acid sequences were determined by FSEC screening, and thereby a stable hChemR23-BRIL fusion protein was obtained. FIG. 1 illustrates a histogram by FSEC of the hChemR23-BRIL fusion protein.

As a result of the FSEC screening, the BRIL fusion protein (SEQ ID NO: 11) in which the 1$^{st}$ to 31$^{st}$ amino acids and the 343$^{rd}$ to 373$^{rd}$ amino acid residues of hChemR23 were deleted, the 252$^{nd}$ leucine was deleted, and BRIL was linked between the 251$^{st}$ arginine and the 253$^{rd}$ alanine of hChemR23 was selected.

Example 2

Preparation of hChemR23-BRIL Fusion Protein

A baculovirus expression system was constructed for the selected mutants by the following procedure. First, among the amino acid sequences of hChemR23 represented by SEQ ID NO: 10, the amino acid sequence in which a histidine tag is added to the C-terminus of the cDNA sequence encoding the amino acid sequences from the 32$^{nd}$ to the 342$^{nd}$ (after deleting the 252$^{nd}$ leucine and inserting BRIL) is encoded, and cDNA consisting of the sequence in which 192$^{nd}$ glutamic acid was substituted with glutamic acid was recombined into a modified pFastBac1 (produced by Invitrogen) to construct an Sf9 cell expression vector (pFastBac1-hChemR23-BRIL).

According to the manual of Bac to Bac Baculovirus Expression System (produced by Invitrogen), the constructed pFastBac1-hChemR23-BRIL vector was transformed into a DH10Bac competent cell to obtain hChemR23-BRIL expression bacmid. The bacmid was transfected into Sf9 cells to produce a recombinant baculovirus. According to the manual, Sf9 cells were infected with the produced baculovirus to prepare Sf9 cells expressing hChemR23-BRIL on the cell membrane.

Cell membrane fractions were prepared from SD cells expressing ChemR23-BRIL on the cell membrane by the following method. Sf9 cells were frozen and thawed, suspended in a hypotonic buffer [10 mmol/L HEPES pH 7.5, 20 mmol/L KCl, 10 mM MgCl$_2$, protein inhibitor cocktail tablet Complete (trademark) EDTA free], transferred to an ultracentrifugation tube, and ultracentrifuged at 45,000 rpm for 30 minutes at 4° C.

The precipitate was suspended with a high osmotic buffer [10 mmol/L HEPES pH 7.5, 10 mmol/L MgCl$_2$, 20 mmol/L KCl, 1M NaCl, protein inhibitor cocktail tablet Complete (trademark) EDTA free], suspended with a Dounce homogenizer (Nippon Genetics Co., Ltd.), and ultracentrifuged again at 45,000 rpm for 30 minutes. The precipitate was resuspended with the high osmotic buffer, suspended in the Dounce homogenizer, and ultracentrifugated again at 45,000 rpm for 30 minutes.

The precipitate was suspended with the high osmotic buffer containing 40% glycerol and stored frozen at −80° C. as an Sf9 cell membrane fraction. After thawing the SD cell membrane containing hChemR23-BRIL on ice, the membrane fraction was suspended in a solubilizing buffer [50 mmol/L HEPES pH 7.5, 500 mmol/L NaCl, 10% glycerol, 2% n-Dodecyl (registered trademark)-D-maltoside (DDM), 0.03% Cholesteryl hemi succinate (CHS), cocktail tablet Complete (Trademark) EDTA free (Roche)] and gently mixed using a rotator at 4° C. for 2 hours so as to solubilize the membrane.

After solubilization, ultracentrifugation was performed at 45,000 rpm for 40 minutes, and the supernatant was recovered. 10 mL of TALON Metal Affinity Resin (produced by Clontech) equilibrated with a Wash buffer (50 mmol/L HEPES pH 7.5, 500 mmol/L NaCl, 10% glycerol, 2% DDM, 0.03% CHS, 20 mmol/L imidazole) was added thereto, and proteins were adsorbed by a batch method at 4° C. for 2 hours.

The resin was packed in an empty column, washed with 5 CV (Column Volume) of a Wash buffer, washed with 5 CV of a Wash buffer having a salt concentration increased to 800 mmol/L, and then eluted with 3 CV of an Elution buffer (50 mmol/L HEPES pH 7.5, 500 mmol/L NaCl, 10% glycerol, 2% DDM, 0.03% CHS, 500 mmol/L imidazole).

The eluted sample was concentrated to 10 mL by ultrafiltration, replaced with a Wash buffer w/o imidazole (50 mmol/L HEPES pH 7.5, 500 mmol/L NaCl, 10% glycerol, 2% DDM, 0.03% CHS) using a PD-10 column, and the required amount of tabacco etch virus protease (TEV) protease was added and allowed to stand at 4° C. overnight.

The next day, after checking cleavage with TEV protease, 6 mL of Ni Sepharose 6 Fast Flow (prepared GE Healthcare Japan) equilibrated with Wash buffer w/o imidazole was added, and proteins were adsorbed by a batch method at 4° C. for 2 hours. The column was filled with a resin, flow-through fraction were collected and concentrated to about 1 mL using Amicon Ultra (100 kDa cut size, manufactured by Merck Millipore), a protein concentration was calculated by BCA assay (Smith, P. K. et al. Anal. Biochem., 1985: 150; 76-85) and $UV_{280}$ measurement, and the $UV_{280}$ was monitored to calculate the subsequent concentration. Finally, it was concentrated to about 30 mg/mL to obtain a purified hChemR23-BRIL sample.

Example 3

Immunity and Subcloning of Antibody-Producing Hybridomas

For use as an antigen, a sample was prepared by reconstitution of purified hChemR23-BRIL into liposomes by the following method.

Purified hChemR23-BRIL was mixed with L-α-phosphatidylcholine (EggPC) solution (10 mg/mL EggPC, 0.8 w/v % Sodium Cholate, 0.5 mg/mL Lipid A in PBS) at a ratio of 1 mg protein with respect to 10 mg lipid. After removing the surfactant by adding Bio-Beads SM-2 (Bio-Rad Laboratories) approximately equal to liquid volume and gently mixing by inversion, a hChemR23-BRIL proteoliposome for immunization was prepared by ultrasonic homogenization.

The liposome antigen for ELISA was mixed in a biotin-PE solution (10 mg/mL EggPC, 25 µg/mL biotinyl PE (Avanti Polar Lipids), 0.8 w/v % sodium cholate in PBS) containing EggPC at a ratio of 1 mg of protein with respect to 10 mg of EggPC, and a hChemR23-BRIL proteoliposome for ELISA was prepared in the same manner as the preparation of liposome antigen for immunization.

For immunization, 5-week-old female immunodeficient mice (MRL/MpJJms, slc-lpr/lpr, Japan SLC, Inc.) were used. In the first immunization, mice were immunized by intraperitoneal injection with the above-described hChemR23-BRIL proteoliposome for immunization diluted with a PBS buffer as an antigen solution.

In the second and subsequent additional immunizations, a mixture of liposome antigen diluted with the PBS buffer and an equal amount of Imject Alum (Thermo Fisher Scientific) was used as an antigen solution. The first immunization (100 µg/mouse), the first additional immunization (50 µg/mouse) 7 days after the first immunization, and the second additional immunization (50 µg/mouse) 21 days after the first immunization were performed.

A serum sample was prepared by a centrifugal operation using blood collected on the $7^{th}$ day after the second immunization, and an antibody titer was measured by a liposome ELISA method. On the $7^{th}$ day after the third immunization, whole blood was collected and splenectomy was performed. A serum sample was prepared from the collected whole blood by a centrifugal operation. Spleen cells were extracted from the extracted spleen and fused with mouse myeloma cells (P3/NS1/1-Ag4-1, JCRB cell bank, National Institute of Biomedical Innovation) by a PEG method.

The hybridoma cells were suspended in a medium in which one bottle of HAT Media Supplement $(50_x)$ Hybri-Max (manufactured by SIGMA-ALDRICH) was added to 500 mL of RPMI1640 (manufactured by Nacalai Tesque), and 300 µL each was dispensed into the 96-well plate and allowed to stand for 1 week under conditions of 37° C. and 5% $CO_2$.

On the $7^{th}$ day after HAT selection, the anti-hChemR 23-BRIL antibody in the culture supernatant of each well was subjected to primary screening by the liposome ELISA method. The wells in which antibody production was observed were suspended, transferred to a 24-well plate, and statically cultured at 37° C. The liposome ELISA method used here was a method in which hChemR23-BRIL-embedded biotinylated liposomes were immobilized on a 96-well plate via streptavidin (Japanese Patent Application No. 2009-110994).

Specifically, the hChemR23-BRIL-embedded biotinylated liposomes were diluted with PBS to be 1 to 10 µg/mL, dispensed into a 96-well streptavidin plate, and then allowed to stand at room temperature for 1.5 hours so that the hChemR23-BRIL-embedded biotinylated liposomes were immobilized. A solid phase antigen solution was removed, and PBS containing 1% BSA (hereinafter, referred to as BSA-PBS) was added at 200 µL per well and allowed to stand at room temperature for 2 hours.

BSA-PBS was removed, 50 µL of hybridoma culture supernatant as a primary antibody was added per well, and a mixture was allowed to stand at room temperature for about 2 hours. The hybridoma culture supernatant was removed and washed with a plate washer. As secondary antibody, 50 µL of anti-mouse IgG-HRP conjugate diluted with 0.5 to 1% BSA-PBS was added per well, and allowed to stand at room temperature for about 1.5 hours. A secondary antibody solution was removed and washed with a plate washer. Thereafter, a product of the HRP reaction substrate tetramethylbenzidine (TMB) was detected at an absorbance of 450 nm.

A secondary screening was performed two days after culture expansion to the 24-well plate. The anti-hChemR23-BRIL antibody in the culture supernatant of each well was detected by the liposome ELISA method. By checking binding to hChemR23-BRIL, hCCR10-BRIL (mutant in which 1st to 39th amino acids and 316th to 362nd amino acids are deleted, 236th to 243rd amino acids are removed, and then BRIL is linked) (SEQ ID NO: 12), empty liposome, and denatured hChemR23-BRIL, cells that produced antibodies with high binding to hChemR23-BRIL and low binding to other samples were selected. The wells in which antibody production was observed were suspended, transferred to the 24-well plate, and statically cultured at 37° C.

In addition, hCCR10-BRIL was expressed in the cell membrane of Pichia pastoris, and after culturing, the microbial cells were frozen and thawed, and a necessary amount of Zymolyase (registered trademark) 100T (manufactured by Nacalai Tesque) was added and the microbial cells were shaken at 30° C. for 1 hour at a low speed of about 100 rpm so as to perform a cell wall digestion reaction. Thereafter, ultrasonic disruption was performed, and the supernatant was collected by high-speed centrifugation at 7,000 rpm for 20 minutes.

The collected supernatant was further ultracentrifuged at 45,000 rpm for 40 minutes, the precipitate was suspended with a high salt buf. (10 mmol/L HEPES pH 7.5, 10 mmol/L MgCl$_2$, 20 mmol/L KCl, 1M NaCl) homogenized with a Dounce homogenizer, and ultracentrifugated again at 45,000 rpm for 30 minutes. After suspending the precipitate in Membrane buf. (50 mmol/L HEPES pH 7.5, 120 mmol/L NaCl, 20% glycerol), an appropriate ligand was added to be 100 μmol/L, and the mixture was used as a membrane fraction. The purification was performed in the same manner as described in Example 2.

The anti-hChemR23-BRIL antibody in the culture cell supernatant selected in the secondary screening was subjected to the tertiary screening by the same FSEC method as in Example 1. A Pichia pastoris cell membrane expressing hChemR23-BRIL and a Pichia pastoris cell membrane expressing hCCR10-BRIL were solubilized with 1% DDM, and ultracentrifugated, and the obtained supernatant was used.

A hybridoma that produced an antibody that binds to both hChemR23-BRIL and hCCR10-BRIL and clearly had stronger binding to hChemR23-BRIL than hCCR10-BRIL was selected and designated as hybridoma SRP2070. When the subclass of the anti-BRIL monoclonal antibody SRP2070 produced by the hybridoma SRP2070 was checked, it was mouse IgG2a class.

Example 4

Preparation of Purified Antibody

The obtained anti-BRIL antibody-producing hybridoma SRP2070 was expansion cultured in a 10 cm dish, and cells per dish were intraperitoneally administered to one nude mouse (BALB/cSlc-nu/nu, Japan SLC, Inc.). Mice were intraperitoneally administered with 500 μL of Freund's Incomplete Adjuvant (FIA, produced by DIFCO) 7 days prior to intraperitoneal administration of the hybridoma. Ascites was collected after cell inoculation. The ascites was centrifuged to remove cells and debris. Then, it filtered with syringe packed with absorbent cotton, and also a residue was filtered.

A saturated ammonium sulfate solution in which 390 g of ammonium sulfate was dissolved in 1 L of PBS buffer was prepared, the ascites and the saturated ammonium sulfate solution were mixed at a volume ratio of 1:2, and stirred at 4° C. for 1 hour or longer. Thereafter, the obtained solution was replaced with the PBS buffer by overnight dialysis.

The purification of the monoclonal antibody was performed with HiTrap protein G (produced by GE Healthcare Japan) using an AKTA pure chromatography system (manufactured by GE Healthcare Japan). Elution was performed with 1 mol/L of glycine hydrochloride buffer, and 1 mol/L of Tris-HCl was added to an elution tube beforehand at one-tenth of the elution amount, so that the eluate was neutralized simultaneously with the elution.

The obtained purified monoclonal antibody is replaced with the PBS buffer, treated with a resin in which papain (produced by Nacalai Tesque) is immobilized to NETS-activated Sepharose 4 Fast Flow (produced by GE Healthcare Japan), and then fragmented into Fab. Then, the Fab was supplied to Protein A Sepharose 4 Fast Flow (produced by GE Healthcare Japan), and the flowthrough fractions were collected so that the Fab fragment was prepared. The obtained Fab fragment sample was designated as Fab antibody SRP2070 Fab for structure analysis.

Example 5

Sequence Analysis of Anti-BRIL Antibody SRP2070 Antibody cDNA was produced from mRNA extracted from the established SRP2070-producing hybridoma, and the amino acid sequences of the heavy and light chains of the antibody and the gene sequences encoding them were analyzed.

As a result, it became clear that a VH region of the SRP2070 antibody consists of the amino acid sequence represented by SEQ ID NO: 7, and the CDR1 to CDR3 of the VH region of the SRP2070 antibody consist of the amino acid sequence represented by SEQ ID NOs: 1 to 3. It became clear that the gene encoding the amino acid sequence represented by SEQ ID NO: 7 is represented by SEQ ID NO: 13. It became clear that the amino acid sequence including the signal sequence is represented by SEQ ID NO: 15, and the gene encoding the amino acid sequence is represented by SEQ ID NO: 17.

```
SEQ ID NO: 7:
QIQLQQSGPELVKPGASVKISCKASGYTFTDFYINWMKQRPGQGLEWIGW
IFPGSGNTHYNEKFKGKATLIVDTSSSTAFMQLNSLTSEDSAVYFCTRPV
SYYDFDYWGQGTTLTVSS (Underline is CDR part)

SEQ ID NO: 1:
DFYIN

SEQ ID NO: 2:
WIFPGSGNTHYNEKFKG

SEQ ID NO: 3:
PVSYYYDFDY
```

In addition, it became clear that a VL region of the SRP2070 antibody consists of the amino acid sequence represented by SEQ ID NO: 8, and the CDR1 to CDR3 of the VL region consist of the amino acid sequence represented by SEQ ID NOs: 4 to 6. It became clear that the gene encoding the amino acid sequence represented by SEQ ID NO: 8 is represented by SEQ ID NO: 14. It became clear that the amino acid sequence including the signal sequence is represented by SEQ ID NO: 16, and the gene encoding the amino acid sequence is represented by SEQ ID NO: 18.

SEQ ID NO: 8:
DIVLTQSPATLSVTPGDRVSLSCRASQSVSNYLHWYQQKSHESPRLLIK
YASQSISGIPSRFSGSGSGTDFTLSINSVETEDFGMYFCQQSNSWPLTF
GAGTKLELR (Underline is CDR part)

SEQ ID NO: 4:
RASQSVSNYLH

SEQ ID NO: 5:
YASQSIS

SEQ ID NO: 6:
QQSNSWPLT

Example 6

Preparation of hChemR23-BRIL/apo/SRP2070 Fab Complex and Structure Analysis

To the hChemR23-BRIL sample prepared by the method described in Example 2, about 1.2 times the molar amount of SRP2070 Fab was added and allowed to stand at 4° C. for 1 hour. The sample was purified with a combination of an AKTA Pure chromatography system (manufactured by GE Healthcare Japan) and Superdex 200 Increase 10/300 GL (manufactured by GE Healthcare Japan).

A peak of the hChemR23-BRIL/apo/SRP2070 Fab complex was collected and concentrated to about 50 mg/mL so as to obtain a sample for crystallization.

The obtained crystallization sample was cocrystallized by a lipidic cubic phase (LCP) method [Martin Caffrey et al., NATURE PROTOCOLS 2009; 4(5): 706-31]. Specifically, the hChemR23-BRIL/apo/SRP2070 Fab complex crystallization sample, 1-oleyl-rac-glycerol, and cholesterol were mixed in a syringe at a ratio of 40%, 54%, and 6% so as to produce a LCP.

For crystallization, using a glass sandwich plate for LCP crystallization, 800 nL of a crystallization solution was dispensed into 50 nL of LCP and sealed with a glass cover.

The crystallization was performed in combination of precipitants such as 20 to 50 v/v % of polyethylene glycol 300, 20 to 50 v/v % of polyethylene glycol 400, 20 to 50 v/v % of polyethylene glycol monomethyl ether 500, or 20 to 50 v/v % of polyethylene glycol dimethyl ether 550; buffers such as 100 mM of MES-NaOH and pH 6 to 6.5, 100 mM of Hepes-NaOH and pH 7 to 7.5, or 100 mM of Tris-HCl and pH 8 to 8.5, additives for organic solvents such as; 0.5 to 2 v/v % of methyl-2,4-pentandiol, 0.5 to 2 v/v % of 2,5-hexanediol, 0.5 to 2 v/v % of 1,2,3-hexanetriol, or 0.5 to 2 v/v % of isopropanol; and salts such as 50 to 400 mM of ammonium acetate, ammonium chloride, ammonium phosphate monobasic, ammonium fluoride, ammonium formate, ammonium citrate dibasic, ammonium phosphate dibasic, ammonium nitrate, ammonium sulfate, ammonium tartrate dibasic, calcium acetate hydrate, calcium chloride dehydrate, lithium acetate dehydrate, lithium chloride, lithium citrate tribasic tetra hydrate, lithium nitrate, lithium sulfate monohydrate, magnesium acetate tetra hydrate, magnesium chloride hexahydrate, magnesium formate dehydrate, magnesium nitrate hexahydrate, magnesium sulfate hydrate, nickel (II) chloride hexahydrate, potassium acetate, potassium chloride, potassium citrate tribasic monohydrate, potassium phosphate monobasic, potassium fluoride, potassium formate, potassium phosphate dibasic, potassium nitrate, potassium sodium tartrate tetra hydrate, potassium sulfate, potassium thiocyanate, sodium acetate trihydrate, sodium chloride, sodium citrate tribasic dehydrate, sodium phosphate monobasic, sodium formate, sodium phosphate dibasic dehydrate, sodium malonate pH 7.0, sodium nitrate, sodium sulfate decahydrate, sodium tartrate dibasic dehydrate, sodium thiocyanate, succinic acid pH 7.0, zinc acetate dehydrate, and zinc sulfate heptahydrate.

Among the above conditions, the crystals of hChemR23-BRIL/apo/SRP2070 Fab were formed in combination with the precipitants such as 36 to 47 v/v % of polyethylene glycol 300, or 32 to 43.5 v/v % of polyethylene glycol monomethyl ether 500, the buffers such as 100 mM of MES-NaOH pH 6 to 6.5, the additives for organic solvents such as 0.5 to 2 v/v % of methyl-2,4-pentandiol or 0.5 to 2 v/v % of 2,5-hexanediol, the salts such as 125 to 190 mM of disodium succinate and 75 to 150 mM of trisodium citrate.

Note that, although a crystallization of the hChemR23-BRIL fusion protein was carried out in the absence of antibody, the crystals were not possible to be obtained under any conditions, and the structural analysis of hChemR23 was not able to be performed. On the other hand, it was possible to produce the crystals in the presence of the anti-BRIL antibody (Table 1).

Figure 2:
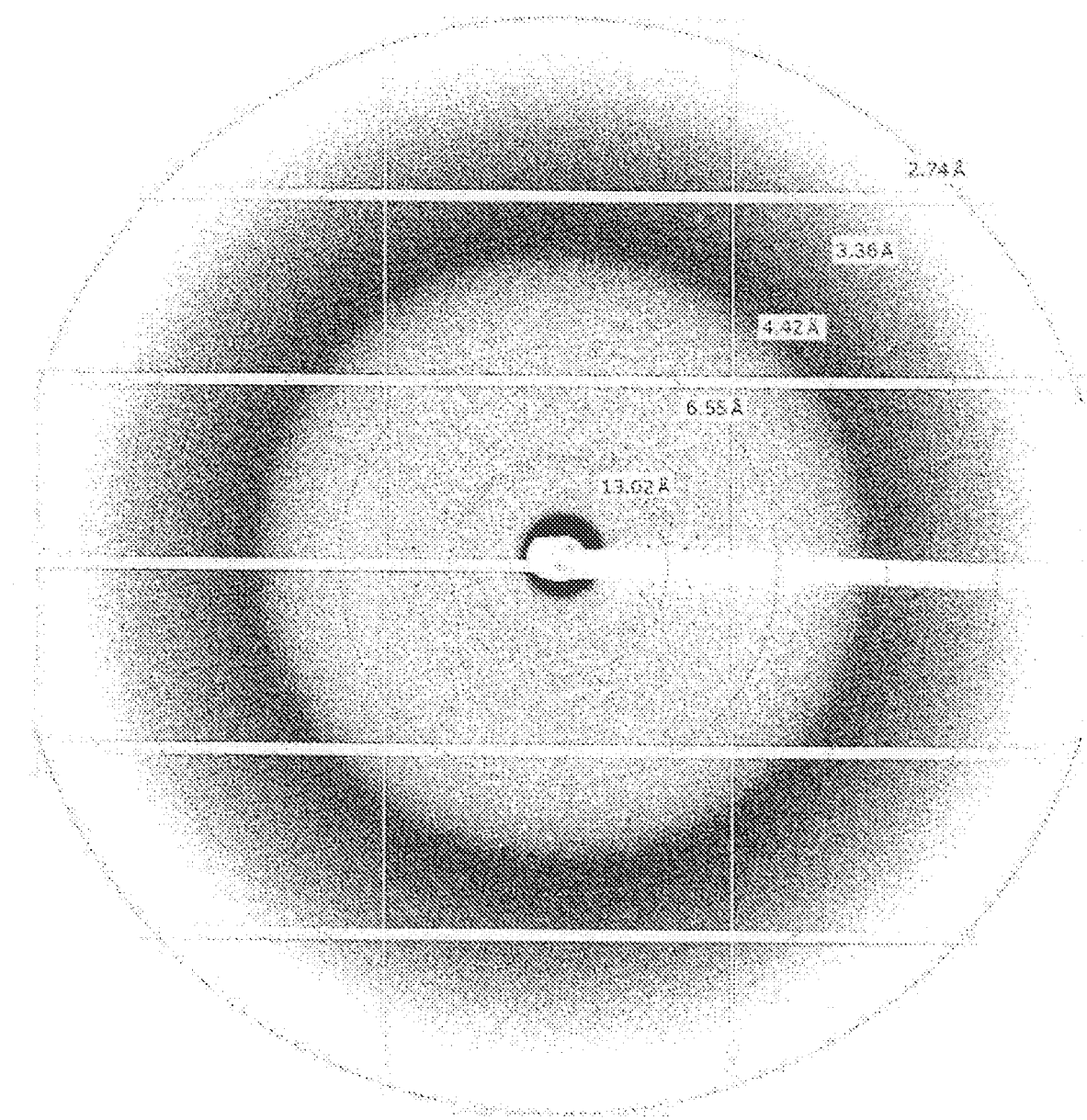
FIG. 2 is a view illustrating an X-ray diffraction image of hChemR23-BRIL/apo/SRP2070 Fab complex crystal.
Figure 3:
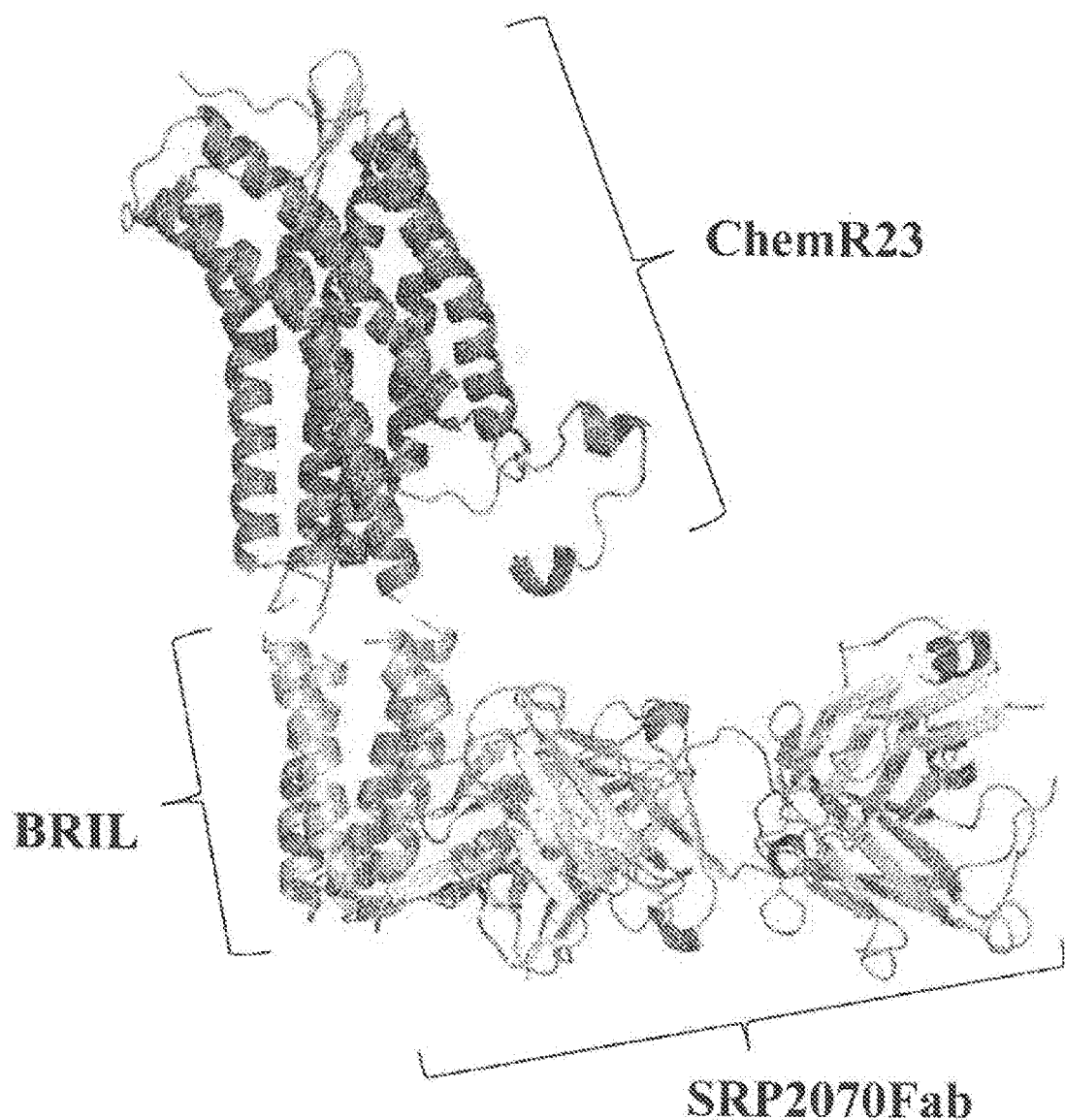
FIG. 3 is a view illustrating a result of structural analysis of the hChemR23-BRIL/apo/SRP2070 Fab complex.

The crystals obtained by the LCP method were frozen in liquid nitrogen and subjected to an X-ray diffraction experiment at the SPring-8 beam line BL32XU, a Japan Syncrotron Radiation Research Institute (JASRI). The crystals with a diffraction power of 4.0 Å resolution were obtained and complete data at 4.5 Å resolution were obtained by merging partial data from a total of 81 crystals to perform a structure analysis of the hChemR23-BRIL/apo/SRP2070 Fab complex. As a result of the structure analysis, a protein three-dimensional structure illustrated in FIG. 3 was obtained. FIG. 2 illustrates the result of the X-ray diffraction image, and FIG. 3 illustrates the result of the structural analysis. Table 1 indicates the results of crystal purification and structural analysis of the BRIL fusion protein using the anti-BRIL antibody.

TABLE 1

Crystal purification and structural analysis of the BRIL fusion protein using the anti-BRIL antibody

|  | hChemR23-BRIL/apo | 5HT$_{1B}$-BRIL/Ergotamine |
| --- | --- | --- |
| Crystal production (absence of antibody) | Not obtained | Obtained (Wang et al., Science 2013; 340: 610-614) |
| Structural analysis (absence of antibody) | Not obtained | Obtained (Wang et al., Science 2013; 340: 610-614) |
| Crystal production (presence of antibody) | Obtained | Obtained |
| Structural analysis (presence of antibody) | Obtained | Obtained |

From the above results, it was found that the BRIL fusion protein, crystals of which was not possible to be obtained in the absence of the anti-BRIL antibody, was possible to be crystallized for the first time in the presence of the anti-BRIL antibody, and that the target protein was possible to be determined the structure.

Example 7

Preparation of Complex of 5HT$_{1B}$-BRIL and SRP2070 Fab and Structural Analysis 5HT$_{1B}$-BRIL was prepared by the same method with the same construct as previously reported (Wang et al., Science 2013; 340: 610-614). Ergotamine, a small molecule ligand, was added by 100 μM when solubilizing the Sf9 cell membrane expressing $5HT_{1B}$-BRIL fusion protein, and purified by adding 100 μM to the buffer of each subsequent purification step, so that the $5HT_{1B}$-BRIL fusion protein was stably purified. A gel filtration fraction containing $5HT_{1B}$-BRIL/SRP2070 Fab prepared by the same method as in Example 6 was concentrated to about 30 mg/mL, and crystallized by the LCP method in the same manner as described in Example 6.

Figure 4:
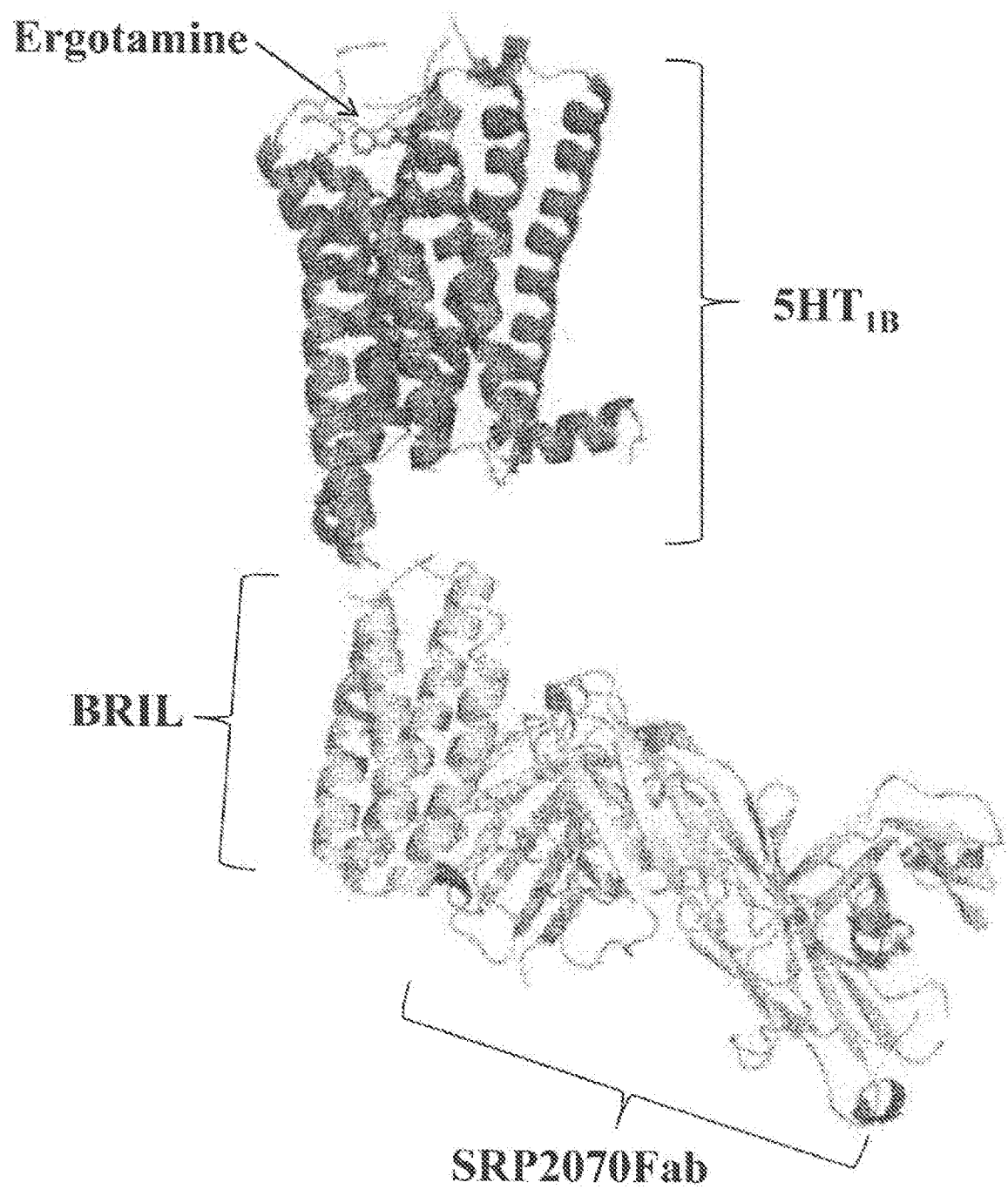
FIG. 4 is a view illustrating a result of structural analysis of a $5HT_{1B}$-BRIL/Ergotamine/SRP2070 Fab complex.

As a result, crystals that can be used for X-ray diffraction data acquisition were formed within one week after crystallization (Table 1). In the same manner as in Example 6, at the SPring-8 beam line BL32XU, JASRI, the crystal was subjected to an X-ray diffraction experiment, and complete data at 3 Å resolution were obtained so as to perform a structure analysis of the $5HT_{1B}$-BRIL/Ergotamine/SRP2070 Fab complex. The results are indicated in FIG. 4 and Table 1.

From the above results, it was possible to obtain excellent crystals in the presence of the anti-BRIL antibody as in Example 6, and thus the anti-BRIL antibody does not inhibit the crystallization of the BRIL fusion protein in the crystallization, but rather allows the anti-BRIL antibody to coexist so that crystallization conditions was possible to be easily found and crystallization was possible to be efficiently performed. Therefore, it was clear that the anti-BRIL antibody of the present invention can stably crystallize the target protein fused with BRIL, and becomes a very useful tool in the structure analysis of the BRIL fusion protein.

Example 8

Preparation and Crystallization of BRIL/SRP2070 Fab

A mutant gene obtained by adding TEV protease recognition amino acid to the N-terminus of the BRIL protein amino acid sequence was inserted into the pET28a vector (produced by Novagen) using restriction enzyme sites BamHI and HindIII, and expressed as a His-tag fusion. The expressed sample was purified by Ni Sepharose 6 Fast Flow (produced by GE Healthcare Japan), and then the His-tag was cleaved with TEV protease.

The cleaved sample was again applied to Ni Sepharose 6 Fast Flow, and the collected flowthrough fractions were purified with an anion exchange column. By using a sample obtained in such a manner that about 1.2 times the amount of SRP2070 Fab at a molar ratio was added to the sample, and the sample was allowed to stand at 4° C. for 1 hour, followed by gel filtration to collect the peak of the BRIL/SRP2070 Fab complex, and concentrate to about 15 mg/mL, the crystallization was performed by the vapor diffusion method.

Specifically, 100 nL of the BRIL/SRP2070 Fab complex protein solution and 100 nL of the crystallization solution are mixed to form a crystallization inner solution, and the crystallization inner solution was sealed together with 50 μL of the crystallization solution (crystallization outer solution), and allowed to stand at 4° C., and thereby the crystals were obtained within one week.

As the crystallization solution, for example, crystals were produced from 18 w/v % of polyethylene glycol 8000, 180 mmol/L of ammonium fluoride, and 50 mmol/L of CHES pH 9.5. The obtained crystals were frozen in liquid nitrogen and subjected to an X-ray diffraction experiment. As a result, complete data at 2.0 Å resolution was obtained, and the BRIL/SRP2070 Fab complex structure was successively determined.

The binding mode of SRP2070 Fab to BRIL was similar to that in the hChemR23-BRIL fusion protein of Example 6 and the $5HT_{1B}$-BRIL fusion protein of Example 7. The epitope and paratope of SRP2070 Fab were determined from the complex structure analysis result of the obtained BRIL and SRP2070 Fab.

When a complex structure of BRIL and the anti-BRIL antibody SRP2070 was checked, it was found that the anti-BRIL antibody SRP2070 recognizes and binds from the third helix structure to the fourth helix structure of BRIL.

As a result of selecting amino acid residues in the BRIL protein interacting with CDR of the anti-BRIL antibody SRP2070 within 4 Å in order to analyze detailed epitopes, it was clear that the anti-BRIL antibody SRP2070 of the present invention binds to the amino acid residues existing from the third helix structure to the fourth helix structure in the three-dimensional structure of the BRIL protein, and the amino acid residues of $67^{th}$ Ile (I), $71^{st}$ Gln (Q), $74^{th}$ Asp (D), $77^{th}$ Lys (K), $78^{th}$ Leu (L), $83^{rd}$ Lys (K), $85^{th}$ Lys (K), $86^{th}$ Glu (E), $88^{th}$ Gln (Q), $89^{th}$ Ala (A), $90^{th}$ Ala (A), $92^{nd}$ Glu (E), 93th Gln (Q), $96^{th}$ Thr (T), $97^{th}$ Thr (T), $99^{th}$ Asn (N), and $100^{th}$ Ala (A) from the N-terminus of the BRIL amino acid sequence were recognized.

Further, among the above epitopes, the $74^{th}$ Asp (D), the $92^{nd}$ Glu (E), the $93^{rd}$ Gln (Q), the $96^{th}$ Thr (T), the $97^{th}$ Thr (T), and the $99^{th}$ Asn (N) were hydrogen-bonded to the antibody, and thus it became clear that they are the most important amino acid residues among the amino acid residues constituting the epitope of anti-BRIL antibody SRP2070.

Example 9

Negative Stain Electron Microscopy of hChemR23-BRIL/apo/SRP2070 Fab

The hChemR23-BRIL fusion protein was prepared by the method described in Example 1. Thereafter, a hChemR23-BRIL/apo/SRP2070 Fab complex was prepared by the method described in Example 6 and adjusted to a concentration of about 2 mg/mL as a sample for negative stain electron microscopy. This sample was diluted 100 times and centrifuged at 18,000 rpm at 4° C. for 15 minutes. 2.5 μL of the supernatant sample was placed on a sample grid and allowed to stand at room temperature for 1 minute to soak the sample in the grid.

Thereafter, the sample solution was removed from the grid and washed with water three times. 2. 5 μL of negative staining reagent NanoW (Methylamine Tungstate, from Nanoprobes) was placed on the sample grid and allowed to stand at room temperature for 1 minute to stain protein particles. Excess staining reagent was wiped off and the sample grid was dried before imaging. A TF20 electron microscope was operated at 200 kV at room temperature, and electron micrographs were taken under the conditions of a magnification of 100,000 (pixel size 1.06 Å/pixel) and focal lengths of 1.8 to 2.5 μm.

Figure 5:
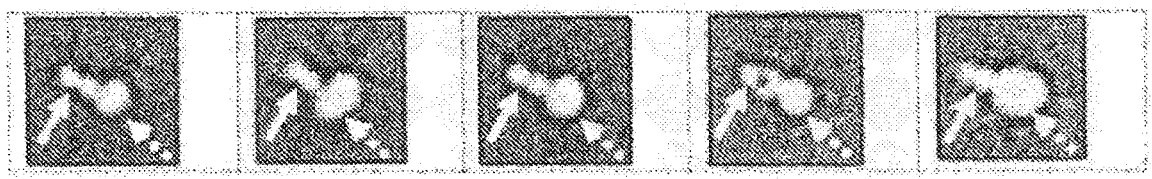
FIG. 5 is a view of a hChemR23-BRIL/apo/SRP2070 Fab complex imaged with an electron microscope. A part indicated by an arrow (solid line) is SRP2070 Fab, and a part indicated by an arrow (broken line) is a GPCR part.

FIG. 5 illustrates the result of classification of two-dimensional images and acquisition of five representative types of averaged images. As illustrated in FIG. 5, a part indicated by an arrow (solid line) is SRP2070 Fab, a part indicated by an arrow (broken line) is a GPCR part, and it was possible to distinguish the direction of the SRP2070 Fab. From the above results, it was clear that by using the anti-BRIL antibody of the present invention to the BRIL fusion protein, the GPCR protein part and the BRIL part in the three-dimensional structure can be distinguished in the liquid phase, and as a result, the orientation of the BRIL fusion protein molecule can be identified.

Example 10

Negative Stain Electron Microscopy of $5HT_{1B}$-BRIL/Ergotamine/SRP2070 Fab $5HT_{1B}$-BRIL/Ergotamine/SRP2070 Fab was prepared by the method described in Example 7. As a change, the concentrations of the surfactants DDM and CHS in the final buffer composition were set to 0.025%. As a negative stain electron microscopy sample, the concentration was adjusted to about 0.75 mg/mL. This sample was diluted 50 times and centrifuged at 18,000 rpm at 4° C. for 15 minutes. 2.5 µL of the supernatant sample was placed on a sample grid and allowed to stand at room temperature for 10 seconds to soak the sample in the grid.

Thereafter, the sample solution was removed from the grid and washed with water three times. 2. 5 µL of negative staining reagent Nano-W (Methylamine Tungstate, from Nanoprobes) was placed on the sample grid and allowed to stand at room temperature for 1 minute to stain protein particles. Excess staining reagent was wiped off and the sample grid was dried before imaging. A TF20 electron microscope was operated at 200 kV at room temperature, and an electron micrograph was taken under the conditions of a magnification of 80,000 (pixel size 1.32 Å/pixel) and a focal length of 1.8 to 2.5 µm.

Figure 6:
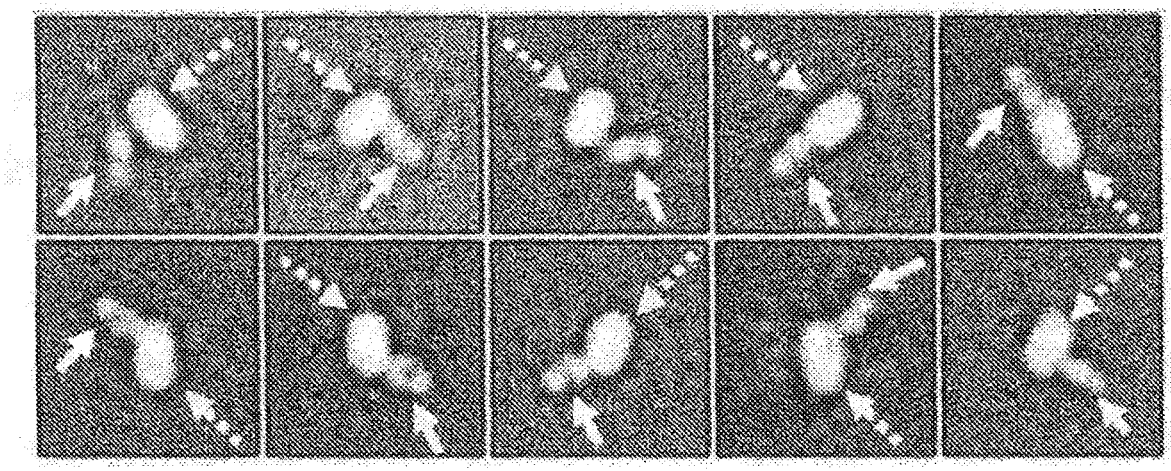
FIG. 6 is a view illustrating results of structural analysis of a $5HT_{1B}$-BRIL/Ergotamine/SRP2070 Fab complex imaged with an electron microscope. A part indicated by an arrow (solid line) is SRP2070 Fab, and a part indicated by an arrow (broken line) is a GPCR part.

FIG. 6 illustrates the result of classification of two-dimensional images and acquisition of ten representative types of averaged images. As illustrated in FIG. 6, a part indicated by an arrow (solid line) is SRP2070 Fab, a part indicated by an arrow (broken line) is a GPCR part, and it was possible to distinguish the direction of the SRP2070 Fab. From the above results, it was clear that by using the anti-BRIL antibody of the present invention to not only the ChemR23-BRIL fusion protein in the Example above, but also other BRIL fusion proteins, the GPCR protein part and the BRIL part in the three-dimensional structure can be distinguished in the liquid phase, and as a result, the orientation of the BRIL fusion protein molecule can be identified.

Although the invention has been described in detail with reference to specific embodiments, it will be apparent to those skilled in the art that various changes and modifications can be made without departing from the spirit and scope of the invention. This application is based on a Japanese patent application filed on Jul. 13, 2017 (Japanese Patent Application No. 2017-137269), which is incorporated by reference in its entirety. Also, all references cited herein are incorporated as a whole.

SEQUENCE LISTING FREE TEXT

SEQ ID NO: 9—Description of artificial sequence: amino acid sequence of BRIL protein
SEQ ID NO: 10—Description of artificial sequence: amino acid sequence of human ChemR23
SEQ ID NO: 11—Description of artificial sequence: amino acid sequence of human ChemR23-BRIL fusion protein
SEQ ID NO: 12—Description of artificial sequence: amino acid sequence of human CCR10-BRIL fusion protein

The invention claimed is:

1. A method of stabilizing a BRIL fusion protein in which BRIL is fused to a target protein, comprising:

reacting an antibody which binds to BRIL or an antigen-binding fragment thereof with the BRIL fusion protein, and stabilizing the BRIL fusion protein by binding the antibody which binds to BRIL or the antigen-binding fragment thereof to BRIL of the BRIL fusion protein, wherein BRIL is a heat resistant apocytochrome b562 modified protein, wherein the BRIL fusion protein is a protein in which two adjacent helix structures of the target protein are fused by BRIL, wherein the target protein is a membrane-expressed protein selected from the group consisting of a G protein-coupled receptor (GPCR), an ion channel, and a transporter, and wherein the antibody which binds to BRIL or the antigen-binding fragment thereof is any one selected from the following (1) to (3):

(1) an antibody which binds to at least any one of a third helix structure and a fourth helix structure of BRIL or an antigen-binding fragment thereof, (2) an antibody which binds to at least a portion of the third helix structure to the fourth helix structure of BRIL or an antigen-binding fragment thereof, and (3) an antibody which binds to at least one amino acid residue selected from amino acid residues of 67th Ile (I), 71st Gln (Q), 74th Asp (D), 77th Lys (K), 78th Leu (L), 83rd Lys (K), 85th Lys (K), 86th Glu (E), 88th Gln (Q), 89th Ala (A), 90th Ala (A), 92nd Glu (E), 93rd Gln (Q), 96th Thr (T), 97th Thr (T), 99th Asn (N), and 100th Ala (A) from an N-terminus of BRIL or an antigen-binding fragment thereof.

2. The method according to claim 1,
wherein the antibody which binds to BRIL or the antigen-binding fragment thereof is any one selected from the following (i) to (iii):
(i) an antibody which binds by competing with an antibody in which complementarity determining regions (CDRs) 1 to 3 of a heavy chain variable region (VH) of the antibody comprise amino acid sequences represented by SEQ ID NOs: 1 to 3, respectively, and in which CDRs 1 to 3 of a light chain variable region (VL) of the antibody comprise amino acid sequences represented by SEQ ID NOs: 4 to 6, respectively, or an antigen-binding fragment thereof,
(ii) an antibody which binds to an epitope to which an antibody in which CDRs 1 to 3 of VH of the antibody comprise the amino acid sequences represented by SEQ ID NOs: 1 to 3, respectively, and in which CDRs 1 to 3 of VL of the antibody comprise the amino acid sequences represented by SEQ ID NOs: 4 to 6, respectively, binds or an antigen-binding fragment thereof, and
(iii) an antibody which binds to the same epitope as an epitope to which an antibody in which CDRs 1 to 3 of VH of the antibody comprise the amino acid sequences represented by SEQ ID NOs: 1 to 3, respectively, and in which CDRs 1 to 3 of VL of the antibody comprise the amino acid sequences represented by SEQ ID NOs: 4 to 6, respectively, binds or an antigen-binding fragment thereof.

3. The method according to claim 1,
wherein the antibody which binds to BRIL or the antigen-binding fragment thereof comprises VH CDRs 1 to 3 represented by SEQ ID NOs: 1 to 3, respectively, and VL CDRs 1 to 3 represented by SEQ ID NOs: 4 to 6, respectively.

4. A method of analyzing a three-dimensional structure of a BRIL fusion protein in which BRIL is fused to a target protein, comprising:

reacting an antibody which binds to BRIL or an antigen-binding fragment thereof with the BRIL fusion protein, and
performing structural analysis on the three-dimensional structure of the BRIL fusion protein,
wherein BRIL is a heat resistant apocytochrome b562 modified protein,
wherein the BRIL fusion protein is a protein in which two adjacent helix structures of the target protein are fused by BRIL,
wherein the target protein is a membrane-expressed protein selected from the group consisting of a G protein-coupled receptor (GPCR), an ion channel, and a transporter, and
wherein the antibody which binds to BRIL or the antigen-binding fragment thereof is any one selected from the following (1) to (3):
(1) an antibody which binds to at least any one of a third helix structure and a fourth helix structure of BRIL or an antigen-binding fragment thereof,
(2) an antibody which binds to at least a portion of the third helix structure to the fourth helix structure of BRIL or an antigen-binding fragment thereof, and
(3) an antibody which binds to at least one amino acid residue selected from amino acid residues of $67^{th}$ Ile (I), $71^{st}$ Gln (Q), $74^{th}$ Asp (D), $77^{th}$ Lys (K), $78^{th}$ Leu (L), $83^{rd}$ Lys (K), $85^{th}$ Lys (K), $86^{th}$ Glu (E), $88^{th}$ Gln (Q), $89^{th}$ Ala (A), $90^{th}$ Ala (A), $92^{nd}$ Glu (E), $93^{rd}$ Gln (Q), $96^{th}$ Thr (T), $97^{th}$ Thr (T), $99^{th}$ Asn (N), and $100^{th}$ Ala (A) from an N-terminus of BRIL or an antigen-binding fragment thereof.

5. The method according to claim 4, wherein the structural analysis is performed using an electron microscope.

6. The method according to claim 4, wherein the structural analysis is X-ray crystallography.

7. The method according to claim 4, wherein the structural analysis is performed using a cryo electron microscope.

* * * * *